United States Patent
Zhang et al.

(10) Patent No.: US 11,951,155 B2
(45) Date of Patent: Apr. 9, 2024

(54) PEA-DERIVED PEPTIDE WITH MUSCLE-BUILDING EFFECT AND PREPARATION METHOD THEREOF, AND DRUG AND USE

(71) Applicant: Zhongshi Duqing(Shandong) Biotech Co., Ltd, Heze (CN)

(72) Inventors: Zhao Zhang, Heze (CN); Jiuxun Zhang, Heze (CN); Zheng Zhang, Heze (CN); Jie Li, Heze (CN); Wei Wei, Heze (CN); Xiping Zhang, Heze (CN); Zhongli Pei, Heze (CN); Shuai Gu, Heze (CN); Lizhu Niu, Heze (CN)

(73) Assignee: Zhongshi Duqing(Shandong) Biotech Co., Ltd, Heze (CN)

( * ) Notice: Subject to any disclaimer, the term of this patent is extended or adjusted under 35 U.S.C. 154(b) by 0 days.

(21) Appl. No.: 17/821,421

(22) Filed: Aug. 22, 2022

(65) Prior Publication Data
US 2023/0293631 A1    Sep. 21, 2023

(30) Foreign Application Priority Data
Mar. 15, 2022  (CN) .......................... 202210248928.6

(51) Int. Cl.
*A61K 38/16*    (2006.01)
*A61P 21/06*    (2006.01)

(52) U.S. Cl.
CPC ............ *A61K 38/168* (2013.01); *A61P 21/06* (2018.01)

(58) Field of Classification Search
CPC .............................. A61K 38/168; A61P 21/06
See application file for complete search history.

(56) References Cited

U.S. PATENT DOCUMENTS

| 8,815,806 B2 * | 8/2014 | Aluko | ..................... A61P 13/12 514/21.8 |
| 2015/0031128 A1 * | 1/2015 | Gupta | .................. C12N 5/0043 435/358 |

OTHER PUBLICATIONS

Odaneth et al., "Controlled protein hydrolysis with immobilized alkaline endo-protease," Journal of Applied Biotechnology & Bioengineering, Feb. 23, 2017, 2(2): 66-76. (Year: 2017).*

Cowling EB, "A Review of Literature of the Enzymatic Degradation of Cellulose and Wood," Agriculture, Jul. 1958, No. 2116. (Year: 1958).*

\* cited by examiner

*Primary Examiner* — Julie Ha
(74) *Attorney, Agent, or Firm* — Kinney & Lange, P.A.

(57) ABSTRACT

A pea-derived peptide with a muscle-building effect and a preparation method thereof, and a drug and use, are disclosed. A pea protein is subjected to enzymatic hydrolysis, and five polypeptides with muscle-building effect are obtained by separation as separate peptide fragments. In an in vitro aging skeletal muscle cell assay, changes are analyzed in a gene expression level of regulatory pathways related to skeletal muscle cell proliferation and differentiation, apoptosis and autophagy, and protein synthesis and degradation. In addition, animal experiments are conducted to study the muscle-building effect and a corresponding mechanism of the pea-derived peptide. This shows that the five polypeptide sequences have a significant muscle-building effect, usable as a polypeptide drug for the treatment of sarcopenia.

15 Claims, 13 Drawing Sheets

Specification includes a Sequence Listing.

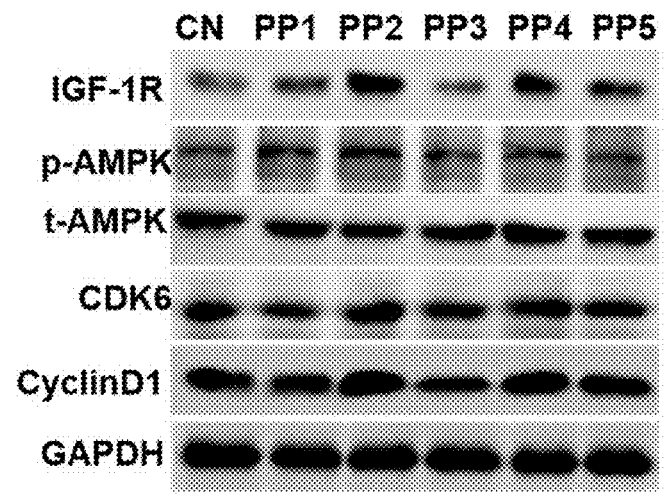
FIG. 7
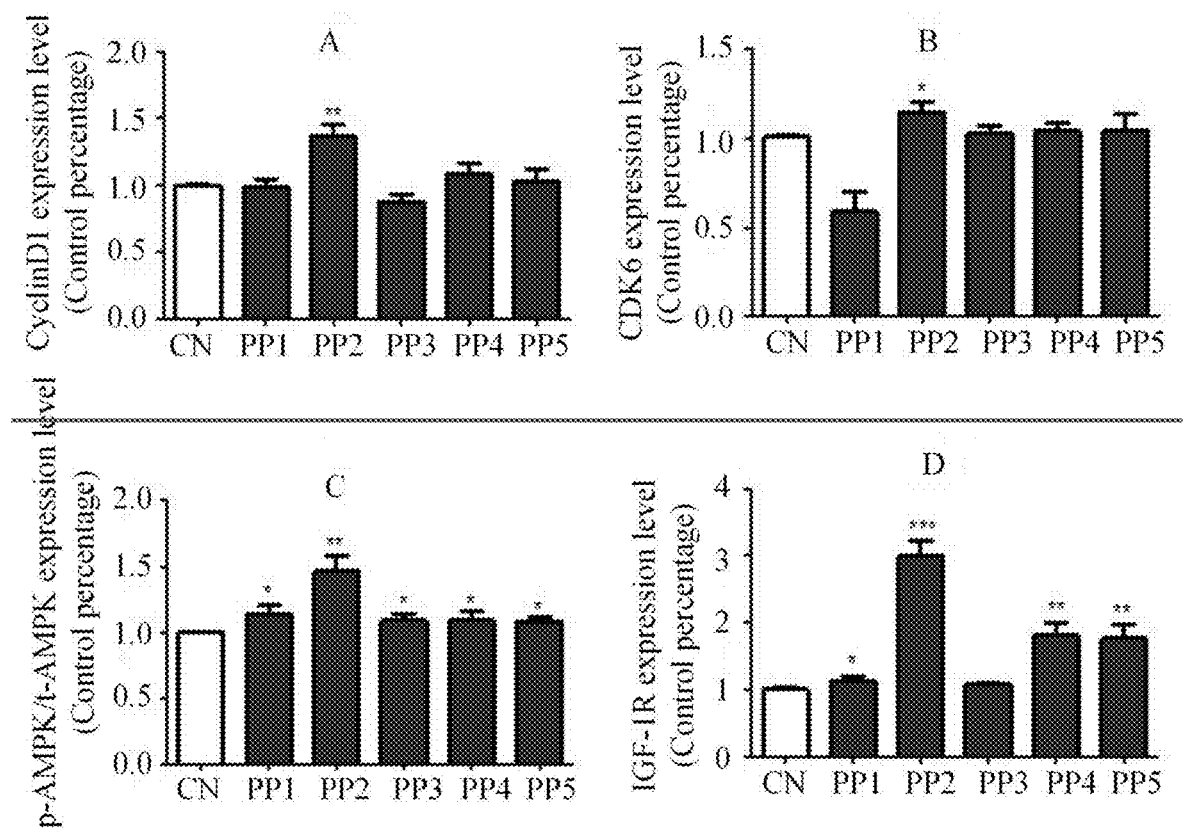

PEA-DERIVED PEPTIDE WITH MUSCLE-BUILDING EFFECT AND PREPARATION METHOD THEREOF, AND DRUG AND USE

CROSS REFERENCE TO RELATED APPLICATION

This patent application claims the benefit and priority of Chinese Patent Application No. 202210248928.6, entitled "Pea-derived Peptide With Muscle-Building Effect and Preparation Method Thereof, and Drug and Use," filed on Mar. 15, 2022, the disclosure of which is incorporated by reference herein in its entirety as part of the present application.

TECHNICAL FIELD

The present disclosure belongs to the technical field of polypeptides, and in particular relates to a pea-derived peptide with muscle-building effect and a preparation method thereof, and a drug and use.

BACKGROUND

Sarcopenia is a syndrome caused by sustained loss of skeletal muscle mass, strength, and function. Skeletal muscle is a driving force of the human motor system. Muscle aging and atrophy are important signs of human aging, causing fractures and joint damages with extremely high probability. Sarcopenia is an age-related disease. The increase of age and the reduction of physical activity level lead to a gradual decline in human muscle mass and strength. Accordingly, muscles of the body cannot maintain balance and agility, which inevitably leads to weakened mobility, making the body sluggish and more likely to fall due to a poor sense of balance. Therefore, the sarcopenia will increase a hospitalization rate and medical expenses, seriously affect a quality of life, and even shorten the lifespan of the elderly people.

At present, the prevention and treatment of sarcopenia mainly includes the following three aspects: (1) exercise therapy can indeed maintain or even increase muscle strength and muscle content; (2) drug intervention treatment can be used; however, there is currently no drug for muscle diseases on the market, and many so-called drugs for preventing and treating sarcopenia are mostly hormones, without fully clarified pros and cons; and (3) nutritional intervention treatment can be used since most of the elderly people have insufficient intake of calories, calcium, protein and vitamin D in their diet structures. In other words, there is a need for a balanced diet rich in nutrients, especially foods including proteins. Insufficient intake of nutrients such as proteins and carbohydrates may increase prevalence of the sarcopenia. In addition, poor nutrient absorption, gastrointestinal diseases, or polypharmacy-caused dietary deficiency, and over-nutrition each play a "fueling" role in the progression of sarcopenia. The aging-caused digestive system degradation results in ineffective absorption and utilization of nutrients in the swallowed food, and the long-term nutrient deficiency may reduce energy supply for activities of the elderly. Moreover, muscle protein degradation is far greater than muscle synthesis capacity, which causes negatively balanced muscle tissue regulation, thereby increasing the muscle burden. Such a vicious circle leads to sarcopenia. Nutrient supplementation such as proteins can effectively prevent and treat pathological changes in muscle mass and muscle function caused by sarcopenia, thus changing the clinical outcomes of patients. Small molecular oligopeptides, due to low sensitization, easy absorption, high absorption rate, and rich amino acid content, can promote muscle protein synthesis to effectively prevent and treat sarcopenia.

Peas are rich in proteins and contain 9 essential amino acids for human body, and rich in branched-chain amino acids; the branched-chain amino acids can promote the release of insulin and growth hormones, and accelerate the utilization of sugar by muscles. However, at present, the types of protein peptides with a muscle-building effect in peas have not been clarified, which limits the development of peptide drugs for the prevention and treatment of sarcopenia.

SUMMARY

In view of this, an object of the present disclosure is to provide a pea-derived peptide with a muscle-building effect and a preparation method and use thereof.

The present disclosure provides a pea-derived peptide with a muscle-building effect, including one or more of the following polypeptides: PP1 with an amino acid sequence shown in SEQ ID NO: 1, PP2 with an amino acid sequence shown in SEQ ID NO: 2, PP3 with an amino acid sequence shown in SEQ ID NO: 3, PP4 with an amino acid sequence shown in SEQ ID NO: 4, and PP5 with an amino acid sequence shown in SEQ ID NO: 5.

Preferably, the pea-derived peptide may include PP2 or a mixture formed by PP2 and the following one or more polypeptides of PP1, PP3, PP4, and PP5.

The present disclosure further provides a preparation method of the pea-derived peptide, including the following steps:
1) conducting enzymatic hydrolysis on a pea protein under an action of an alkaline protease to obtain a first enzymatic hydrolysate;
2) conducting enzymatic hydrolysis on the first enzymatic hydrolysate under an action of papain and cellulase to obtain a second enzymatic hydrolysate;
3) inactivating the second enzymatic hydrolysate, then filtering inactivated second enzymatic hydrolysate through a ceramic membrane, filtering through an organic membrane, and collecting a permeate to obtain a pea-derived peptide;
4) subjecting the pea-derived peptide to gel chromatography, and collecting a fraction S2 at a first pre-determined time interval;
5) subjecting the fraction S2 to separation and purification by preparative liquid chromatography, and collecting a fraction W5 at a second pre-determined time interval; and
6) subjecting the fraction W5 to separation and purification by analytical liquid chromatography, and collecting 5 polypeptide fragments at a PP1 time interval, a PP2 time interval, a PP3 time interval, a PP4 time interval, and a PP5 time interval, respectively, to obtain PP1, PP2, PP3, PP4, and PP5.

Preferably, in step 4), the gel chromatography may be conducted by:
using ultrapure water as an eluent in a chromatographic column.

Preferably, in step 5), the separation and purification by preparative liquid chromatography may be specifically conducted using a preparative liquid chromatographic column at a predetermined flow rate using a mobile phase A comprising a trifluoroacetic acid aqueous solution and a mobile phase B comprising a trifluoroacetic acid acetonitrile solution; and a gradient elution process including the steps of:
  eluting from 0 min to 10 min, with a volume percentage of the mobile phase A decreased from 100% to 90%, and a volume percentage of the mobile phase B increased from 0 to 10%;
  eluting from 10 min to 20 min, with a volume percentage of the mobile phase A decreased from 90% to 50%, and a volume percentage of the mobile phase B increased from 10% to 50%;
  eluting from 20 min to 60 min, with a volume percentage of the mobile phase A decreased from 50% to 10%, and a volume percentage of the mobile phase B increased from 50% to 90%;
  eluting from 60 min to 65 min, with a volume percentage of the mobile phase A increased from 10% to 95%, and a volume percentage of the mobile phase B decreased from 90% to 5%.

Preferably, in step 6), the separation and purification by analytical liquid chromatography may be specifically conducted under the following conditions: a chromatographic column at a predetermined flow rate using a mobile phase A comprising a trifluoroacetic acid aqueous solution, and mobile phase B comprising a trifluoroacetic acid acetonitrile solution; and gradient elution process including the steps of:
  eluting from 0 min to 5 min, with a volume percentage of the mobile phase A decreased from 95% to 90%, and a volume percentage of the mobile phase B increased from 5% to 10%;
  eluting from 5 min to 55 min, with a volume percentage of the mobile phase A decreased from 90% to 15%, and a volume percentage of the mobile phase B increased from 10% to 85%; and
  eluting from 55 min to 60 min, with a volume percentage of the mobile phase A increased from 15% to 95%, and a volume percentage of the mobile phase B decreased from 85% to 5%.

In step 3), the second enzymatic hydrolysate may be filtered through a ceramic membrane of 3,000 Da and filtered through an organic membrane of 1 KDa.

In step 4), the first pre-determined time interval may be 12 min to 18 min.

In step 5), the second pre-determined time interval may be 55 min to 63 min.

In step 6), the PP1 time interval may be 14.444 min, the PP2 time interval may be 18.110 min, the PP3 time interval may be 20.906 min, the PP4 time interval may be 22.973 min, and the PP5 time interval may be 24.462 min.

In step 4), the gel chromatography may be conducted using ultrapure water as an eluent for elution at 2.5 mL/min for 2 h by using a Sephadex G50 chromatographic column of 600 mm×25 mm under a detection wavelength of 214 nm.

In step 5), the preparative liquid chromatographic column may be a 550 mm×40 μm column with a particle size of 20 μm, the predetermined flow rate may be 15 mL/min, the trifluoroacetic acid aqueous solution may have a volume concentration of 0.1%, and the trifluoroacetic acid acetonitrile solution may have a volume concentration of 0.1%.

In step 6), the separation and purification by analytical liquid chromatography may be conducted using a Gemini-NX 10 μm C18 100 A 4.6×250 mm chromatographic column, the predetermined flow rate may be 15 mL/min, the trifluoroacetic acid aqueous solution may have a volume concentration of 0.1%, and the trifluoroacetic acid acetonitrile solution may have a volume concentration of 0.1%. The chromatographic column may be operated at a flow rate of 1.0 mL/min with an injection volume of 10 μL, and an absorbance wavelength of 220 nm.

The present disclosure further provides use of the pea-derived peptide or a pea-derived peptide prepared by the preparation method in preparation of a drug for preventing and/or treating sarcopenia.

Preferably, the drug may have pharmaceutical effects of at least one of promoting myoblast proliferation, activating growth and proliferation signaling pathways in myoblasts, increasing testosterone levels in males, increasing expression of skeletal muscle regeneration regulatory factors, increasing ATPase activity in skeletal muscle mitochondria, or activating insulin signaling pathways.

The present disclosure further provides a drug for preventing and/or treating sarcopenia, where active ingredients of the drug may include the pea-derived peptide or a pea-derived peptide prepared by the preparation method.

Preferably, the drug may be an oral preparation.

In the present disclosure, the pea-derived peptide with a muscle-building effect includes one or more of the following polypeptides: PP1 with an amino acid sequence shown in SEQ ID NO: 1, PP2 with an amino acid sequence shown in SEQ ID NO: 2, PP3 with an amino acid sequence shown in SEQ ID NO: 3, PP4 with an amino acid sequence shown in SEQ ID NO: 4, and PP5 with an amino acid sequence shown in SEQ ID NO: 5. In an in vitro aging skeletal muscle cell assay, changes are analyzed in a gene expression level of regulatory pathways related to skeletal muscle cell proliferation and differentiation, apoptosis and autophagy, and protein synthesis and degradation, and five oligopeptide sequences capable of repairing aging muscles are screened from the pea-derived peptide; in addition, animal experiments are conducted to study the muscle-building effect and a corresponding mechanism of the pea-derived peptide. The results show that the five polypeptide sequences have a significant muscle-building effect, and are expected to be developed as a novel polypeptide drug for the treatment or prevention of sarcopenia. Moreover, the pea-derived peptide has a small molecular weight, easy absorption, high content of branched-chain amino acids, and food safety.

BRIEF DESCRIPTION OF THE DRAWINGS

FIG. 7 shows results of pea-derived peptide samples up-regulating expression of growth and proliferation-related proteins in C2C12 cells in the examples of the present disclosure;

FIG. 8A shows a statistical analysis of a cyclinD1 expression level (control percentage); FIG. 8B shows a statistical analysis of a CDK6 expression level (control percentage); FIG. 8C shows a statistical analysis of a p-AMPK/t-AMPK expression level (control percentage); FIG. 8D shows a statistical analysis of an IGF-1R expression level (control percentage); and the control percentage refers to a ratio of the expression level of the proteins in each group to the expression level of the corresponding protein in the CN group, taking the expression level of CN group as 1;

DETAILED DESCRIPTION OF THE EMBODIMENTS

Figure 1:
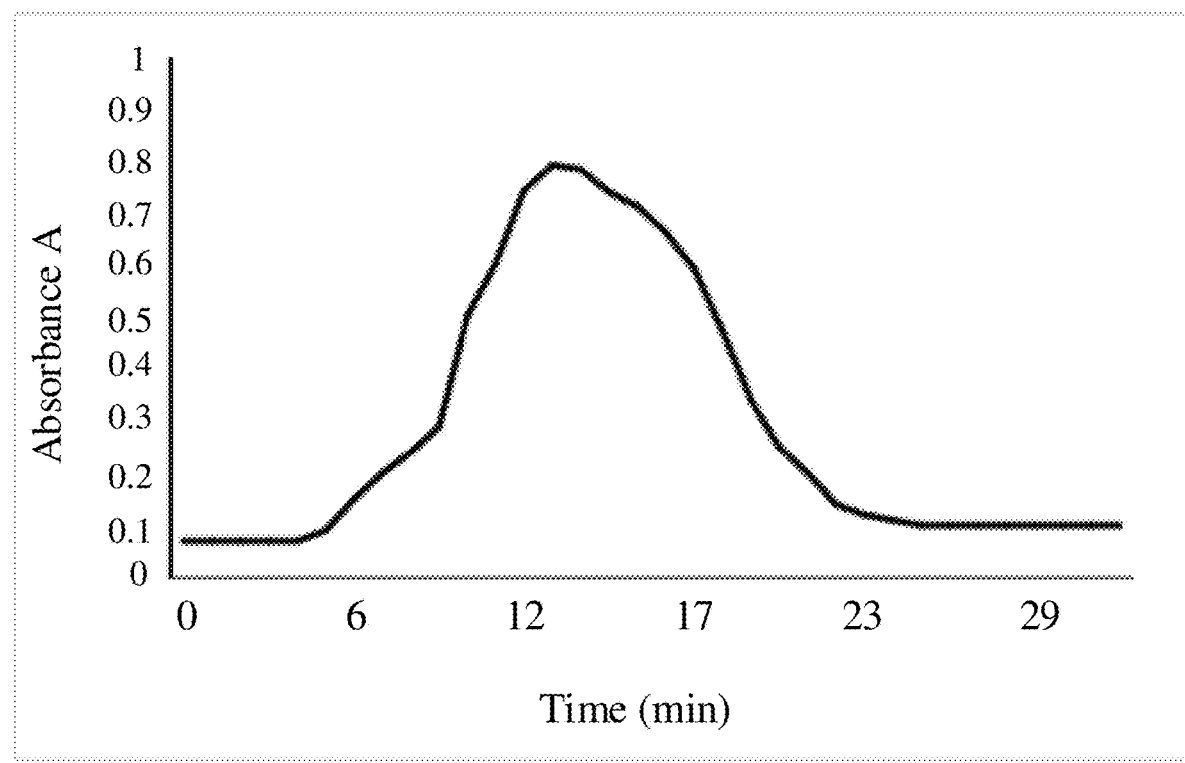
FIG. 1 shows a chromatogram of the pea-derived peptide in the examples of the present disclosure.

The present disclosure provides a pea-derived peptide with a muscle-building effect, including one or more of the following polypeptides: PP1 with an amino acid sequence shown in SEQ ID NO: 1, PP2 with an amino acid sequence shown in SEQ ID NO: 2, PP3 with an amino acid sequence shown in SEQ ID NO: 3, PP4 with an amino acid sequence shown in SEQ ID NO: 4, and PP5 with an amino acid sequence shown in SEQ ID NO: 5.

In the present disclosure, treating skeletal muscle cells with PP1, PP2, PP3, PP4, or PP5 alone can significantly promote cell proliferation, activate growth and proliferation-related signaling pathways in cells, and significantly increase expression of IGF-1R, cyclinD1, CDK6 and p-AMPK. Compared with other pea-derived peptides, PP2 has an optimal muscle-building effect. Therefore, the pea-derived peptide includes preferably PP2 or a mixture of PP2 and one or more of the following polypeptides: PP1, PP3, PP4, and PP5, such as PP2+PP1, PP2+PP3, PP2+PP4, PP2+PP5, PP2+PP1+PP3, PP2+PP1+PP4, PP2+PP1+PP5, PP2+PP3+PP4, PP2+PP3+PP5, PP2+PP3+PP1+PP4, PP2+PP3+PP1+PP5, PP2+PP3+PP1+PP5+PP4.

The present disclosure further provides a preparation method of the pea-derived peptide, including the following steps:
1) conducting enzymatic hydrolysis on a pea protein under the action of an alkaline protease to obtain a first enzymatic hydrolysate;
2) conducting enzymatic hydrolysis on the first enzymatic hydrolysate under the action of papain and cellulase to obtain a second enzymatic hydrolysate;
3) inactivating the second enzymatic hydrolysate, then filtering inactivated second enzymatic hydrolysate through a ceramic membrane of 3,000 Da, filtering through an organic membrane of 1 KDa, and collecting a permeate to obtain a pea-derived peptide;
4) subjecting the pea-derived peptide to gel chromatography, and collecting a fraction S2 at 12 min to 18 min;
5) subjecting the fraction S2 to separation and purification by preparative liquid chromatography, and collecting a fraction W5 at 55 min to 63 min; and
6) subjecting the fraction W5 to separation and purification by analytical liquid chromatography, and collecting 5 polypeptide fragments at 14.444 min, 18.110 min, 20.906 min, 22.973 min, and 24.462 min, respectively, to obtain PP1, PP2, PP3, PP4, and PP5 in sequence.

In the present disclosure, enzymatic hydrolysis is conducted on the pea protein under the action of the alkaline protease to obtain the first enzymatic hydrolysate.

A mass of the alkaline protease accounts for 1.5% to 2.5%, more preferably 2% of a mass of the pea protein. The alkaline protease is preferably added twice: before adding the pea protein, the alkaline protease is added, at 60% to 70% of a total amount; and the remaining alkaline protease is added after adding the pea-derived peptide. The enzymatic hydrolysis by the alkaline protease is conducted at 52° C. to 57° C. and at preferably 65 rpm for 2.5 h to 3.5 h in a system with a pH value of 9. The alkaline protease has an enzymatic activity of preferably 3 million U/mg. In the examples, the alkaline protease is purchased from Shandong LongKete Enzyme Preparation Co., Ltd.

In the present disclosure, enzymatic hydrolysis is conducted on the first enzymatic hydrolysate under the action of the papain and the cellulase to obtain the second enzymatic hydrolysate.

The mass of the papain accounts for 0.8% to 1.2%, more preferably 1% of the mass of the pea protein. The mass of the cellulase accounts for 0.8% to 1.2%, more preferably 1% of the mass of the pea protein. The papain has an enzymatic activity of preferably 1 million U/mg. In the examples, the papain is purchased from Nanning Doing-higher Bio-tech Co., Ltd. The cellulase has an enzymatic activity of preferably 5 million U/mg. In the examples, the cellulase is purchased from Shandong LongKete Enzyme Preparation Co., Ltd. The enzymatic hydrolysis by the papain and the cellulase is conducted at preferably 50° C. to 55° C., more preferably 55° C. for preferably 1.5 h to 2.5 h, more preferably 2 h.

In the present disclosure, enzyme inactivation is conducted on the second enzymatic hydrolysate, followed by filtering the second enzymatic hydrolysate through a ceramic membrane of 3,000 Da, the obtained permeate is filtered through the organic membrane of 1 KDa, and the permeate is collected to obtain the pea-derived peptide.

There is no special limitation on enzymatic hydrolysis method, and enzymatic hydrolysis methods well known in the art can be used. In the examples, the enzyme inactivation is conducted by preferably high-temperature and short-term enzyme inactivation, for example, by conducting at 110° C. for 5 min, which is conducive to inactivating the enzyme in the system and terminating the enzymatic hydrolysis.

After the enzyme inactivation, heating is conducted to room temperature, following the membrane permeation. The collected filtrate is spray-dried to obtain the pea-derived peptide, using a conventional method.

In the present disclosure, the pea-derived peptide is subjected to gel chromatography, and a fraction S2 at 12 min to 18 min is collected.

The gel chromatography is conducted preferably by using ultrapure water as an eluent for elution at 2.5 mL/min for 2 h by using a Sephadex G50 chromatographic column of 600 mm×25 mm at a detection wavelength of 214 nm. After the gel chromatography, fractions are collected at three time points, namely S1 (6 min to 12 min), S2 (12 min to 18 min), and S3 (18 min to 24 min). A skeletal muscle cell culture and proliferation experiment shows that the fractions S1 to S3 can promote the proliferation of cells; and the fraction S2 has an optimal cell proliferation effect, indicating that the fraction S2 has the best muscle-building effect.

In the present disclosure, the fraction S2 is subjected to separation and purification by preparative liquid chromatography and a fraction W5 at 55 min to 63 min is collected.

In the present disclosure, the conditions for separation and purification by preparative liquid chromatography preferably are: preparative liquid chromatographic column: 550 mm×40 and particle size: 20 μm and flow rate: 15 mL/min; mobile phase A: trifluoroacetic acid aqueous solution with a volume concentration of 0.1%, and mobile phase B: trifluoroacetic acid acetonitrile solution with a volume concentration of 0.1%; and gradient elution is conducted as follows:

Eluting from 0 min to 10 min, with a volume percentage of the mobile phase A decreased from 100% to 90%, and a volume percentage of the mobile phase B increased from 0 to 10%;
eluting from 10 min to 20 min, with a volume percentage of the mobile phase A decreased from 90% to 50%, and a volume percentage of the mobile phase B increased from 10% to 50%;
eluting from 20 min to 60 min, with a volume percentage of the mobile phase A decreased from 50% to 10%, and a volume percentage of the mobile phase B increased from 50% to 90%;
eluting from 60 min to 65 min, with a volume percentage of the mobile phase A increased from 10% to 95%, and a volume percentage of the mobile phase B decreased from 90% to 5%.

After the separation and purification by preparative liquid chromatography, seven fractions are collected at 23 min to 31 min (W1), 31 min to 39 min (W2), 39 min to 47 min (W3), 47 min to 55 min (W4), 55 min to 63 min (W5), 63 min to 71 min (W6), and 71 min to 79 min (W7). A muscle-building effect experiment shows that the fraction W5 has the best muscle-building effect.

In the present disclosure, the fraction W5 is subjected to separation and purification by analytical liquid chromatography, and 5 polypeptide fragments are collected at 14.444 min, 18.110 min, 20.906 min, 22.973 min, and 24.462 min, respectively, to obtain PP1, PP2, PP3, PP4, and PP5 in sequence.

In the present disclosure, the conditions for separation and purification by analytical liquid chromatography preferably are: column: Gemini-NX 10 μm C18 100 A, 4.6×250 mm, and flow rate: 15 mL/min; mobile phase A: trifluoroacetic acid aqueous solution with a volume concentration of 0.1%, and mobile phase B: trifluoroacetic acid acetonitrile solution with a volume concentration of 0.1%; flow rate: 1.0 mL/min, injection volume: 10 μL, and absorbance wavelength: 220 nm; and gradient elution is conducted as follows:

elution from 0 min to 5 min, with a volume percentage of the mobile phase A decreased from 95% to 90%, and a volume percentage of the mobile phase B increased from 5% to 10%;
elution from 5 min to 55 min, with a volume percentage of the mobile phase A decreased from 90% to 15%, and a volume percentage of the mobile phase B increased from 10% to 85%; and
elution from 55 min to 60 min, with a volume percentage of the mobile phase A increased from 15% to 95%, and a volume percentage of the mobile phase B decreased from 85% to 5%.

In the present disclosure, PP1, PP2, PP3, PP4, and PP5 are subjected to cell proliferation experiments. Compared with the CN group, the cell concentrations of PP1, PP2, PP3, PP4, and PP5 sample groups increase significantly; and PP2 sample group has the best effect on promoting the proliferation of C2C12 cells, indicating that PP2 sample group has the best muscle-building effect. Meanwhile, results of animal-level experiment show that a mixed group of pea-derived peptide formed by PP1, PP2, PP3, PP4, and PP5 and PP2 group each can improve the forelimb grip force of mice; and the effect of PP2 is better than that of the muscle-building protein powder group and the mixed pea-derived peptide group.

Based on the muscle-building effect of pea-derived peptide, the present disclosure further provides use of the pea-derived peptide or a pea-derived peptide prepared by the preparation method in preparation of a drug for preventing and/or treating sarcopenia.

In the present disclosure, the drug has preferably pharmaceutical effects of promoting myoblast proliferation, activating growth and proliferation signaling pathways in myoblasts, increasing testosterone levels in males, increasing expression of skeletal muscle regeneration regulatory factors, increasing ATPase activity in skeletal muscle mitochondria, and activating insulin signaling pathways. The activation growth and proliferation signaling pathways in myoblasts preferably includes increasing the expression of IGF-1R, cyclinD1, CDK6, and p-AMPK. Testosterone is very closely related to muscle growth, and high-level testosterone can significantly reduce protein degradation. Therefore, increasing testosterone levels in males can promote muscle growth. Increase of expression of skeletal muscle regeneration regulatory factors is conducted preferably by increasing the content of IGFBP-3. Mitochondria are the main place to synthesize ATP, and ATP is the energy required for body movement. A high-energy phosphate bond may be hydrolyzed by an ATP hydrolase to generate a free ATP to provide energy for body activities. Increasing ATPase activity in skeletal muscle mitochondria is beneficial to provide a large amount of free ATP to provide energy for body activities. Insulin (IGFs) signaling pathway is important in muscle growth and damage repair. The activation of insulin signaling pathways is conducted preferably by significantly increasing the expression of IGF-1R, thereby promoting the binding of IGF-1 and IGF-1R, and further promoting the phosphorylation of AMPK. In addition, the up-regulation of cell cycle-related proteins cyclinD1 and CDK6 are induced, which eventually leads to cell proliferation.

The present disclosure further provides a drug for preventing and/or treating sarcopenia, where active ingredients of the drug may include the pea-derived peptide or a pea-derived peptide prepared by the preparation method of the present invention.

The drug is preferably an oral preparation. There is no special limitation on a type of the oral preparation, and types of oral preparations well known in the art can be used, such as oral liquid, tablets, and pills. There is no special limitation on content of the pea-derived peptide in the oral preparation, as long as the daily intake of 1.0 g/kg body weight of mice is ensured.

The pea-derived peptide with a muscle-building effect and the preparation method thereof, and the drug and the use provided in the present disclosure will be described in detail below with reference to examples, but these examples cannot be understood as limiting the claimed scope of the present disclosure.

Example 1

A production method of pea-derived peptide included the following steps:

Step 1: 10,000 L of deionized water was added to an enzymolysis tank, a pH value was adjusted to 9.0 with 10 mol/L NaOH solution, 10 kg of alkaline protease was added, stirring was conducted at 65 r/min during this period, and heating was conducted to about 55° C. by steam.

Step 2: 700 kg of pea-derived protein was fed within 30 min under stirring; after the feeding, the pH value was adjusted to 9.0 with 10 mol/L NaOH solution, 4 kg of alkaline protease was added, and the enzymatic hydrolysis was continued for 3 h.

Step 3: after 3 h of enzymatic hydrolysis by alkaline protease, 1% papain (7.0 kg) and 0.1% cellulase (0.7 kg) were added, and the enzymatic hydrolysis was continued for 2 h.

Step 4: two proteases and the cellulase were inactivated by heating the solution in step 3 to 110° C. and keeping for 5 min.

Step 5: an enzyme-inactivated solution obtained in step 6 was cooled to 50° C., passed through a 30,000 Da ceramic membrane, a filtrate I was collected, and passed through a 1-KDa organic membrane, a filtrate II was collected and spray-dried to obtain the pea-derived peptide.

Determination indexes of the basic physical and chemical properties of the pea-derived peptide: protein content determination (GB5009.9), moisture content determination (GB5009.3), and ash content determination (GB5009.4).

TABLE 1

Determination results of basic physical and chemical properties of pea-derived peptide

| Protein content (%) | Moisture (%) | Ash content (%) |
|---|---|---|
| 89.6 | 5.1 | 5.3 |

Example 2

Separation and Purification, and Identification of Muscle-Building Activity for Pea-Derived Peptide 1. Gel Chromatography 10 g of the pea-derived peptide prepared in Example 1 was dissolved in 200 ml of a 2% acetic acid solution under stirring for 0.5 h. The pea-derived peptide was centrifuged at 8,000 r/min and 15° C. for 15 min, and then filtered through a filter head with a pore size of 0.45 μm for later use.

Sephadex G50 chromatographic column separation: the column was equilibrated with ultrapure water, rinsed for 4 column volumes and the samples were loaded, and the column was flushed with the ultrapure water at 2.5 mL/min for 2 h. The filtered pea-derived peptides by membrane were collected based on the chromatographic peaks, and each obtained fraction was concentrated and freeze-dried into powder with a vacuum drier. The separation was conducted by: using ultrapure water as an eluent for and eluting at 2.5 mL/min for 2 h by using the Sephadex G50 chromatographic column of 600 mm×25 mm under a detection wavelength of 214 nm. FIG. 1 shows a chromatogram. After the gel chromatography, fractions were collected at three time intervals, namely: S1 (6 min to 12 min), S2 (12 min to 18 min), and S3 (18 min to 24 min). The effects of different fractions on the growth of skeletal muscle cells were compared, and the most effective fraction was selected for further separation and purification.

The C2C12 cells in a logarithmic growth phase were inoculated into a 96-well plate; the cells were divided into 4 groups, namely a blank control group (CN, without any peptide fractions), a pea-derived peptide S1 group, a pea-derived peptide S2 group, and a pea-derived peptide S3 group; each treatment group was set to duplicate 3 wells, with approximately 1,000 cells per well. Except for the blank control group, 0.4 μg/ml pea-derived peptide was added to the cells, and 10 μL of a CCK-8 solution was added separately at 0 h, 12 h, 24 h, 36 h, and 48 h, and mixed well; the cells were incubated in a $CO_2$ incubator at 37° C. for 2 h, an OD value was measured using a microplate reader at 450 nm, and a cell proliferation curve was drawn.

Figure 2:
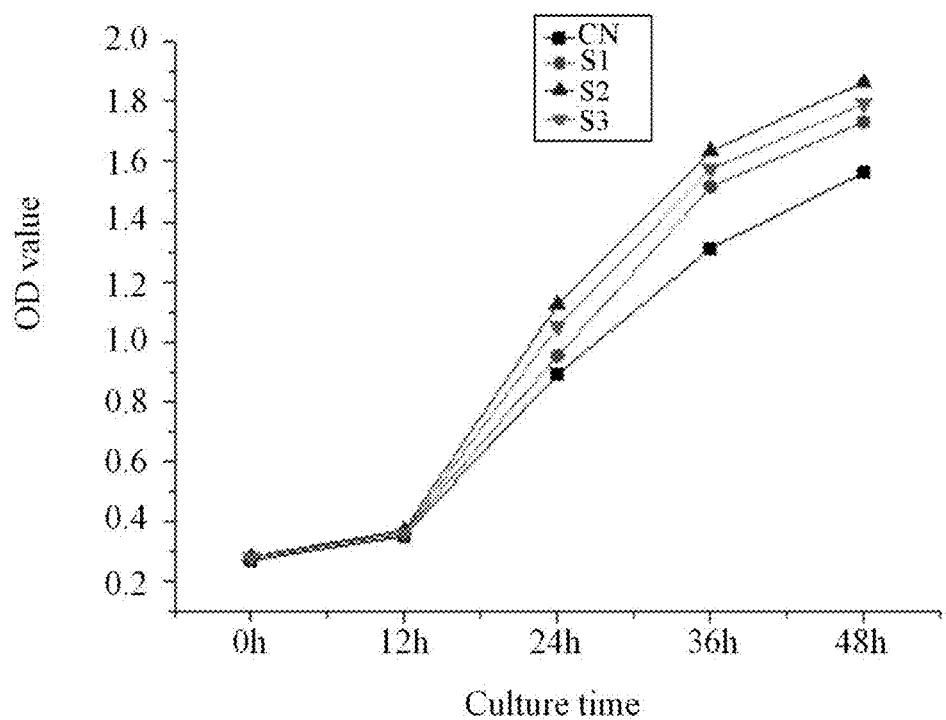
FIG. 2 shows results of promoting skeletal muscle cell proliferation by different fractions (S1, S2, and S3) obtained after gel chromatography in the examples of the present disclosure.
Figure 3:
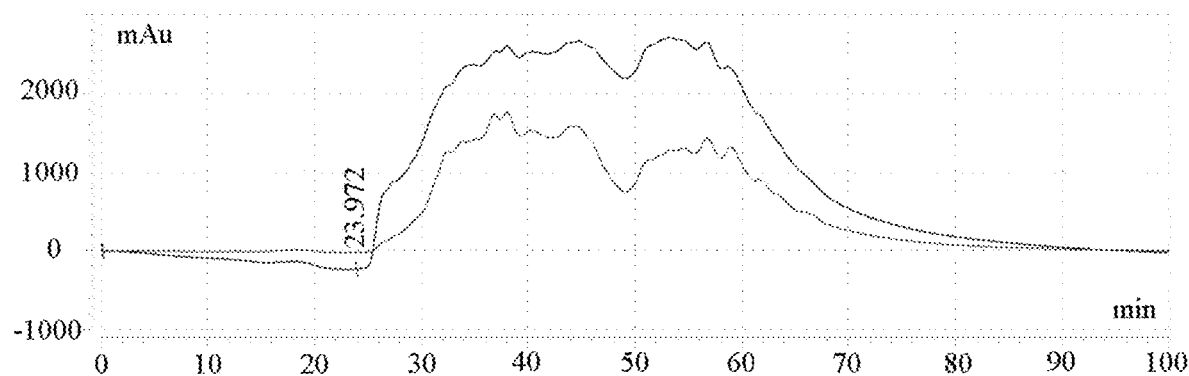
FIG. 3 shows an analysis result of the fraction S2 by preparative liquid chromatography in the examples of the present disclosure.

The muscle-building effects of the three fractions after gel chromatography were compared, and the results are shown in FIG. 2. The OD value represents a cell concentration, and a higher OD value means more C2C12 cells, indicating that the muscle-building effect is better. The results in FIG. 2 show that compared with the blank control group, the fractions 51, S2 and S3 all significantly promote the proliferation of myoblasts C2C12. The fraction S2 promotes the proliferation of myoblasts C2C12 very well and has the best muscle-building effect (FIG. 2). The fraction S2 was further separated and purified by preparative liquid chromatography and fractions with a better muscle-building effect were screened and further separated and purified by analytical liquid chromatography. Chromatographic conditions: gradient elution was conducted by a preparative liquid chromatographic column (550 mm×40 particle size 20 μm), at a flow rate of 15 mL/min, with a mobile phase A (water+0.1% trifluoroacetic acid) and a mobile phase B (acetonitrile+0.1% trifluoroacetic acid). The elution procedure is shown in Table 2. FIG. 3 shows a preparative liquid chromatogram. After the separation and purification by preparative liquid chromatography, seven fractions were collected at 23 min to 31 min (W1), 31 min to 39 min (W2), 39 min to 47 min (W3), 47 min to 55 min (W4), 55 min to 63 min (W5), 63 min to 71 min (W6), and 71 min to 79 min (W7). The effects of the seven fractions on the growth of skeletal muscle cells were detected separately, and a fraction with better muscle-building effect was selected for further study, and further separated and purified by analytical liquid chromatography; meanwhile, a blank control group was set (CN, without adding any peptide fractions).

TABLE 2

Elution conditions of preparative liquid chromatography

| Time | Mobile phase A | Mobile phase B |
|---|---|---|
| 0-10 min | 100-90% | 0-10% |
| 10-20 min | 90-50% | 10-50% |
| 20-60 min | 50-10% | 50-90% |
| 60-65 min | 10-95% | 90-5% |
| 65-100 min | 95% | 5% |

Figure 4:
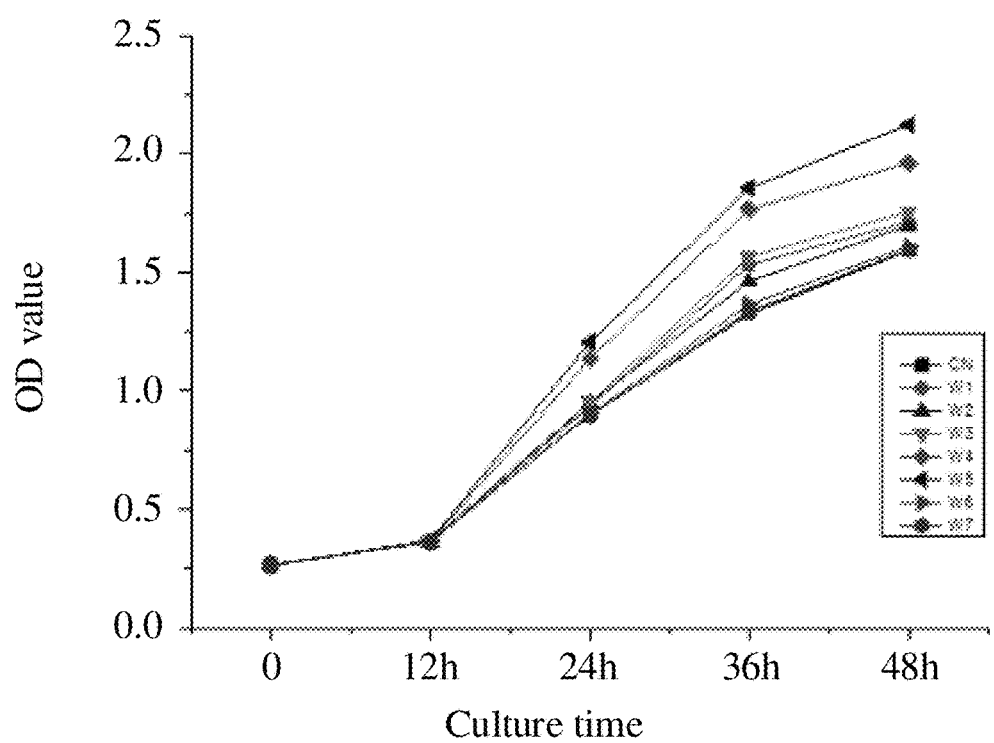
FIG. 4 shows results of promoting skeletal muscle cell proliferation by different fractions (W1 to W7) analyzed through the preparative liquid chromatography in the examples of the present disclosure.
Figure 6:
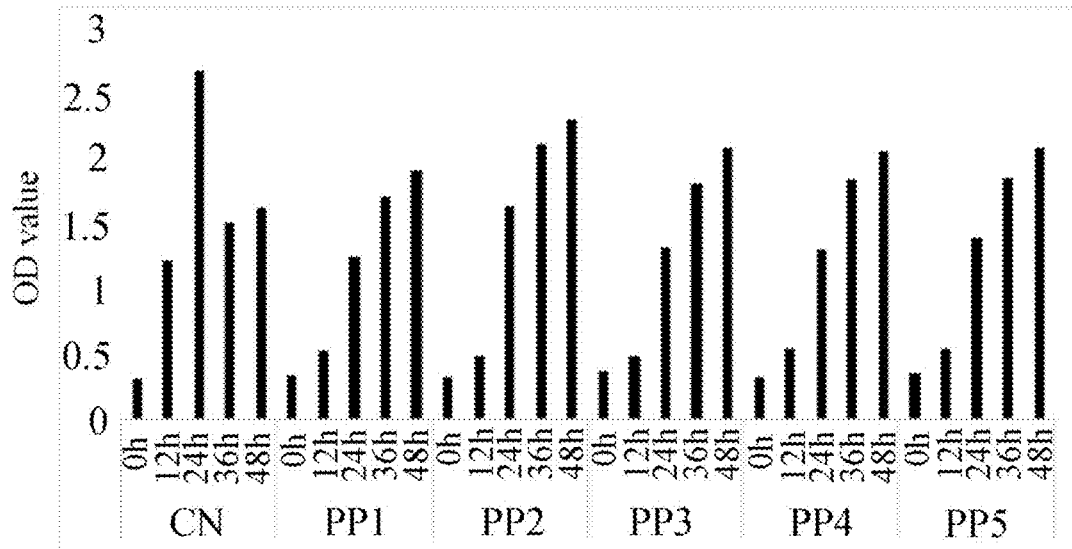
FIG. 6 shows results of pea-derived peptides (P1 to P5) promoting proliferation of C2C12 cells in the examples of the present disclosure, where *$P<0.05$ indicates that a ratio of cell proliferation results in a CN group at a corresponding time is significantly different.
Figure 8A:
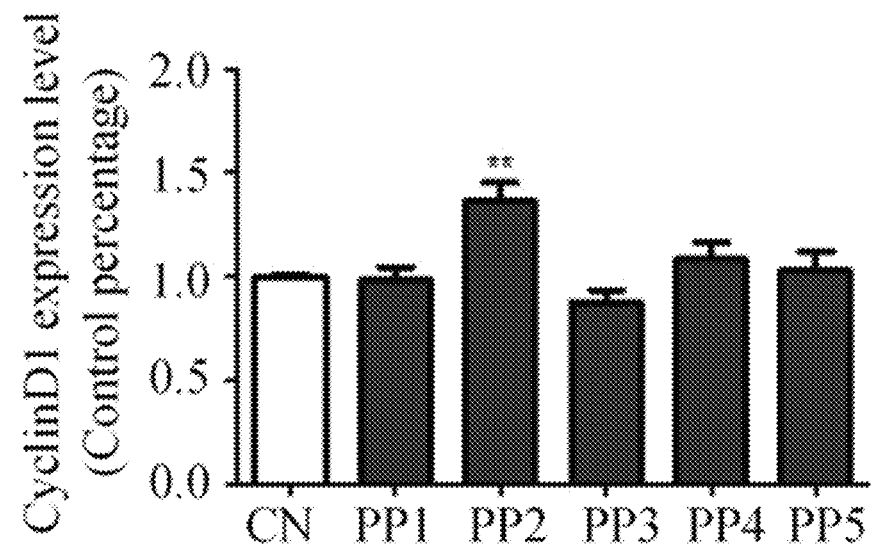
FIG. 8A-FIG. 8D show a statistical result of the pea-derived peptide samples up-regulating the expression of growth and proliferation-related proteins in the C2C12 cells in the examples of the present disclosure; where
Figure 8B:
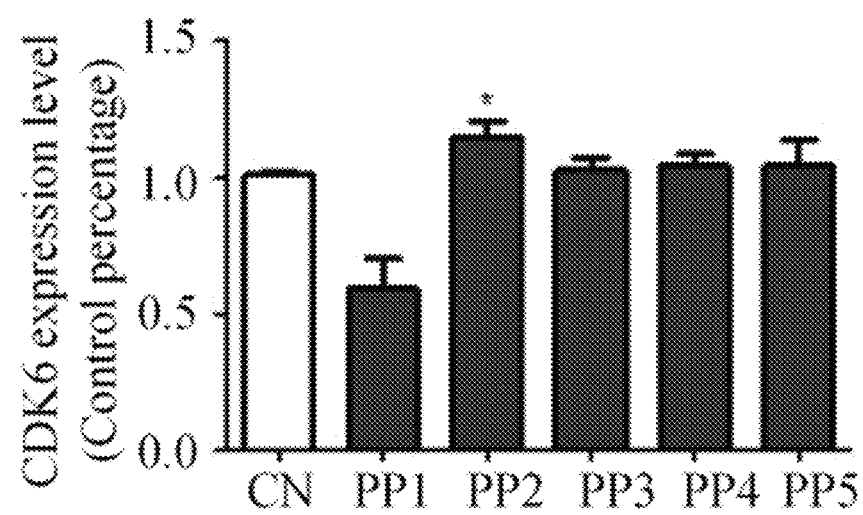
Figure 8C:
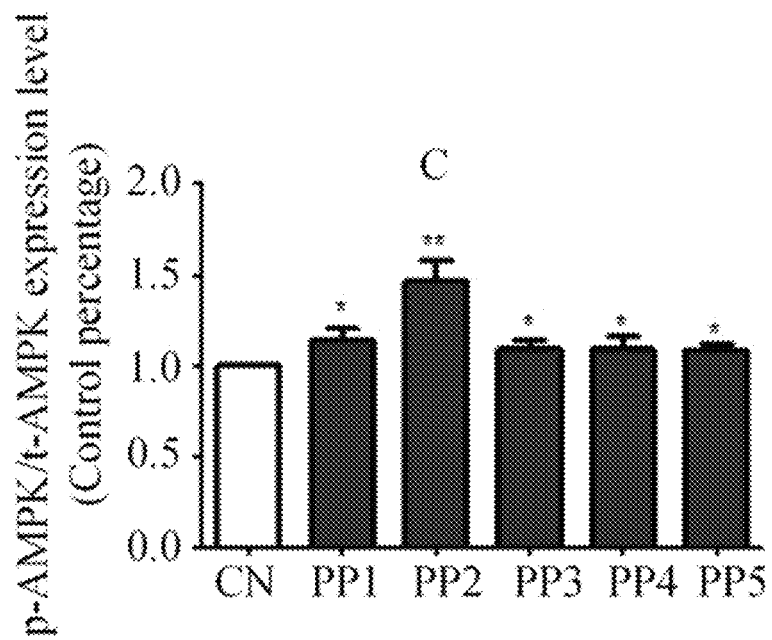
Figure 8D:
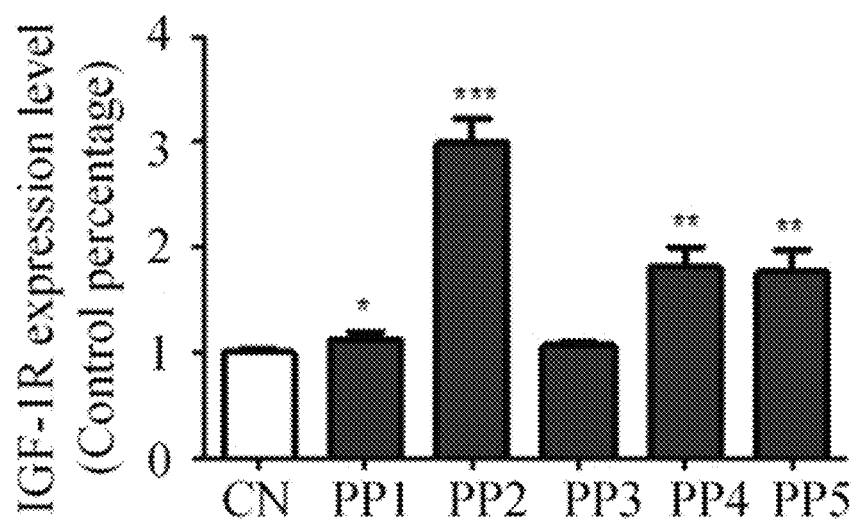

The muscle-building effects of the seven fractions after preparative liquid chromatography were compared, and the results are shown in FIG. 4. The OD value represents a cell concentration, and a higher OD value means more cells, indicating that the muscle-building effect is better. The results in FIG. 4 show that, compared with the blank control group, both fractions W4 and W5 significantly promote the proliferation of myoblasts C2C12; the fraction W5 has best effect on promoting the proliferation of myoblasts C2C12 and has best muscle-building effect. The fraction W5 was further separated and purified by analytical liquid chromatography, and a fraction with better muscle-building effect was screened. An amino acid composition of the fraction was further identified by high-resolution mass spectrometry. Chromatographic conditions: gradient elution was conducted by a Gemini-NX 10 μm C18 100 A chromatographic column (4.6×250 mm), at a flow rate of 15 mL/min, with a mobile phase A (water+0.1% trifluoroacetic acid) and a mobile phase B (acetonitrile+0.1% trifluoroacetic acid). The elution procedure is shown in Table 3, with a flow rate of 1.0 mL/min, an injection volume of 10 μL, and an absorbance of 220 nm. FIG. 6 shows results of the analytical liquid chromatography. Five fractions were obtained, 14.444 min (P1), 18.110 min (P2), 20.906 min (P3), 22.973 min (P4), and 24.462 min (P5), and effects of the five fractions on the growth of skeletal muscle cells were analyzed separately. Further research was conducted on a fraction with a better muscle-building effect.

TABLE 3

Mobile phase gradients for analytical liquid chromatography

| Time | Mobile phase A | Mobile phase B |
|---|---|---|
| 0 min | 95% | 5% |
| 60 min | 35% | 65% |

Further, the purity and structure identification of the obtained pea-derived peptides P1, P2, P3, P4, and P5 were conducted using a nano liter-scale liquid chromatography-Q EXACTIVE mass spectrometry system.
1. Detection conditions:
    (1) mobile phase: phase A: 100% purified water+0.1% formic acid; phase B: 100% acetonitrile+0.1% formic acid;
    (2) flow rate of the mobile phase: 300 nL/min;
    (3) Injection volume: 1 μL of supernatant;
    (4) Gradient elution procedure of the mobile phases as shown in Table 4.

TABLE 4

Gradient elution procedure of the mobile phases

| Time (min) | 0 | 2.0 | 36.0 | 38.0 | 41.0 | 42.0 | 45.0 |
|---|---|---|---|---|---|---|---|
| A (%) | 97 | 97 | 63 | 10 | 10 | 97 | 97 |
| B (%) | 3 | 3 | 37 | 90 | 90 | 3 | 3 |

Figure 5:
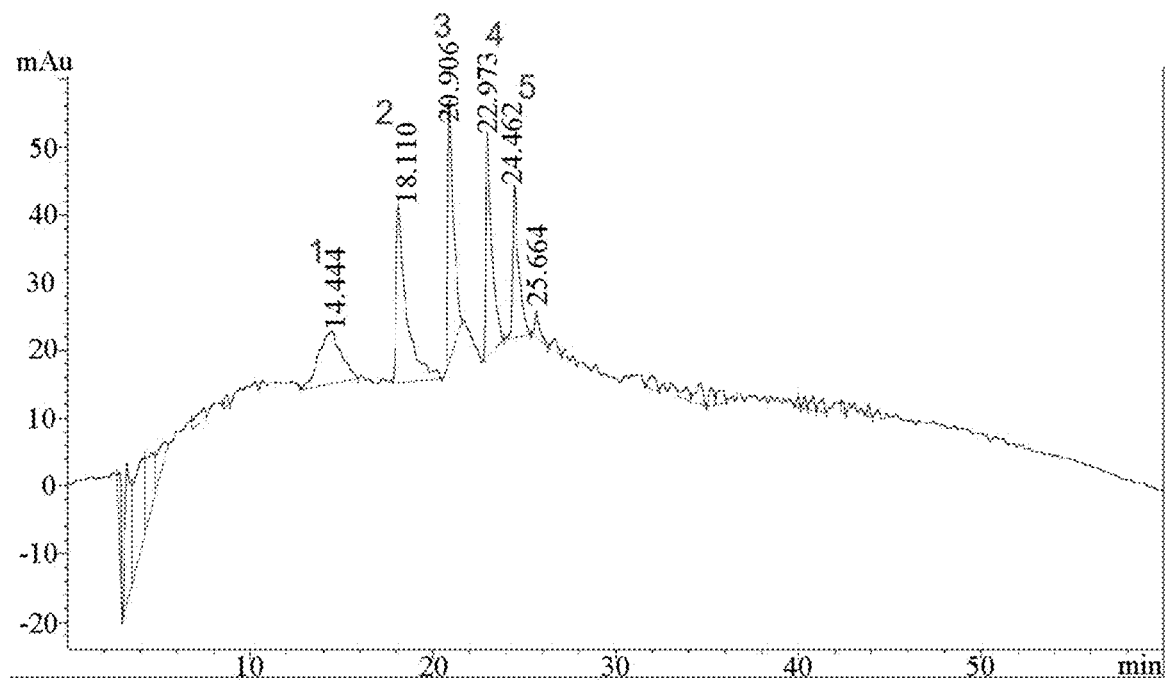
FIG. 5 shows a spectrogram of the fraction W5 obtained through analytical liquid chromatography in the examples of the present disclosure.

The structures of the five fractions were identified by the nano liter-scale liquid chromatography-Q EXACTIVE mass spectrometry, and the results (FIG. 5) were as follows. The sequences of the five protein peptides were Glu-Gly-Ser-Leu-Leu-Leu-Pro-His (EGSLLLPH), Leu-Asp-Leu-Pro-Val-Leu (LDLPVL), Leu-Leu-Tyr-Val-Ile-Arg (LLYVIR), Thr-Asn-Tyr-Glu-Glu-Ile-Glu-Lys-Val-Leu-Leu (TNYEEIEKVLL), and Asn-Thr-Asn-Tyr-Glu-Glu-Ile-Glu-Lys-Val-Leu (NTNYEEIEKVL), respectively. After alignment in NCBI, the sources of the five protein peptides are shown in Table 5.

TABLE 5

Sequence identification of muscle-building structures of pea-derived peptides

| Pea-derived peptide components | Amino acid sequences | Source of sequence |
|---|---|---|
| 1 (PP1) | Glu-Gly-Ser-Leu-Leu-Leu-Pro-His (EGSLLLPH, SEQ ID NO: 1) | P13918\|VCLC_PEA |
| 2 (PP2) | Leu-Asp-Leu-Pro-Val-Leu (LDLPVL, SEQ ID NO: 2) | tr\|O24294\|O24294_PEA:P14594\|LEGB_PEA:P05692\|LEGJ_PEA:P05693\|LEGK_PEA |
| 3 (PP3) | Leu-Leu-Tyr-Val-Ile-Arg (LLYVIR, SEQ ID NO: 3) | tr\|Q9TOP5\|Q9TOP5_PEA:P15838\|LEGA2_PEA:tr\|Q41036\|Q41036_PEA |
| 4 (PP4) | Thr-Asn-Tyr-Glu-Glu-Ile-Glu-Lys-Val-Leu-Leu (TNYEEIEKVLL, SEQ ID NO: 4) | tr\|D3VNE1\|D3VNE1_PEA:tr\|D3VNE2\|D3VNE2_PEA |
| 5 (PP5) | Asn-Thr-Asn-Tyr-Glu-Glu-Ile-Glu-Lys-Val-Leu (NTNYEEIEKVL, SEQ ID NO: 5) | tr\|D3VNE1\|D3VNE1_PEA:tr\|D3VNE2\|D3VNE2_PEA |

Example 3

Effects of PP1, PP2, PP3, PP4, and PP5 on the growth of skeletal muscle cells

1. Materials and Methods

PP1, PP2, PP3, PP4, and PP5 used in experiments were synthesized by Wuhan Xinghao Pharmaceutical Co., Ltd.

Cell Lines and Culture

In this experiment, the cell lines and cultures included a cell line used was C2C12 cells purchased from China Center for Type Culture Collection (CCTCC); fetal bovine serum (FBS), high-glucose DMEM, and 0.25% trypsin were purchased from Gibco; penicillin-streptomycin mixture, PBS buffer, 4% paraformaldehyde, and Triton X-100 were purchased from Solaibio; a cell culture plate and cell culture flasks were purchased from Corning; a CCK-8 kit was purchased from Nanjing Jiancheng Biological Co., Ltd.; and a PVDF membrane was purchased from Merck Millipore.

Culture of C2C12 Cells

The C2C12 cells were taken out from a liquid nitrogen tank, thawed quickly in a 37° C. water bath, the supernatant was discarded after centrifugation, the cells were resuspended in a complete medium (10% FBS+1% penicillin-streptomycin+high-glucose DMEM), and inoculated in a petri dish. When the cell confluence reached 80% to 90%, passage was conducted, and the cell medium was changed every 2 days.

Cell Proliferation Assay

The C2C12 cells in a logarithmic growth phase were inoculated into a 96-well plate; the cells were divided into 6 groups, namely a blank control group (CN, without any peptide fractions), and sample groups including a pea-derived peptide PP1 group (PP1), a pea-derived peptide PP2 group (PP2), a pea-derived peptide PP3 group (PP3), a pea-derived peptide PP4 group (PP4), and a pea-derived peptide PP5 group (PP5). Each treatment group was set to 3 duplicate wells, with approximately 1,000 cells per well. A sample having a concentration of 0.4 μg/ml was added to the cells of the sample groups, and 10 μL of a CCK-8 solution was added separately at 0 h, 12 h, 24 h, 36 h, and 48 h, and mixed well; the cells were incubated in a $CO_2$ incubator at 37° C. for 2 h, an OD value was measured using a microplate reader at 450 nm, and a cell proliferation curve was drawn.

Related Protein Expression Detected by Western Blots

The C2C12 cells in a logarithmic growth phase were inoculated into a 6-well plate at $1 \times 10^6$; the cells were divided into 6 groups, namely a blank control group (CN), and sample groups including a pea-derived peptide PP1 group (PP1), a pea-derived peptide PP2 group (PP2), a pea-derived peptide PP3 group (PP3), a pea-derived peptide PP4 group (PP4), and a pea-derived peptide PP5 group (PP5). Each treatment group was set to duplicate 3 wells, with approximately 1,000,000 cells per well; a sample having a concentration of 0.4 μg/ml was added to the cells of the sample groups, and each treatment group was set to 3 duplicate wells. After co-incubating for 24 h, the cells in different treatment groups were collected, fully lysed, and a total protein was extracted, and a protein concentration was determined using a nucleic acid protein analyzer. The protein sample was mixed with a loading buffer thoroughly, denatured at 100° C. for 10 min, and subjected to SDS-PAGE gel electrophoresis. The program included: 80 V for 30 min; 100 V for 80 min. Membrane transfer was conducted, where the membrane transfer procedure was conducted at 100 V for 90 min. After transferring, the sample was placed in a 5% skimmed milk powder, and sealed in a shaker at room temperature for 1 h. GAPDH antibody (1:2000) and PCNA antibody, AMPK antibody, p-AMPK antibody, IGF-1 antibody (1:1000) were added separately, and allowed to stand at 4° C. overnight. A secondary antibody (1:20000) was added, and incubated at room temperature for 1 h. The membrane was washed 3 times with TBST, and a Pierce-enhanced luminescent agent was added, and exposure was conducted by an automatic exposure machine.

2. Results

Five pea-derived peptides can significantly promote the proliferation of C2C12 cells.

Polypeptides are easier to be digested and absorbed than whole proteins, and can be absorbed and utilized by cells. For example, Lingling Huang et al. reported that thymopentin can be absorbed and utilized by macrophages (Lingling Huang, Ting Xie, and Ningsheng Liang. Study on the Effect of Thymopentin on the Phagocytosis of Rat Peritoneal Macrophages, 2016, 11(3): 346-349). For example, Qun Feng et al. reported that antibacterial peptides can be absorbed and utilized by HTC-8 cells (Qun Feng, Zhong Tian, Jiamin Gao, Xiaoju Li et al. The Isolation and Purification of Antibacterial Peptides from Black Soldier Flies and the Inhibitory Effect of Active Components on the Proliferation of HTC-8 cells. *Journal of Medical Postgraduates*, 2022, 35(1): 17-19). For another example, Na Li et al. reported that cod swimming bladder-derived collagen peptide can be absorbed and utilized by 2BS cells (Na Li et al., The Protective Effect of Cod Swimming Bladder-derived Collagen Peptide on $H_2O_2$-induced early senescence of 2BS cells. *Journal of Chinese Institute of Food Science and Technology*, 2021, 21(11): 101-103). For another example, Shun Li et al. reported the effect of tumstatin 19-peptide on the proliferation and apoptosis of SK-Hep-1 cells (Shun Li et al., The Effects of Tumstatin 19-peptide on the Proliferation and Apoptosis of SK-Hep-1 Cells. *Contemporary Medicine*, 2022, 29 (2): 42-44). In the present disclosure, the five oligopeptides are all small molecule peptides, which can pass through the cell membrane and enter the cytoplasm, thereby activating a series of intracellular signaling pathways.

Results are shown in Table 6.

TABLE 6

Effects of different polypeptide fractions on proliferation of C2C12 cells

| Group | Treatment time | Repeated three groups | | | Average value |
|---|---|---|---|---|---|
| CN | 0 h | 0.32 | 0.27 | 0.38 | 0.32 |
| | 12 h | 0.41 | 0.37 | 0.46 | 1.24 |
| | 24 h | 0.92 | 0.78 | 1.02 | 2.72 |
| | 36 h | 1.53 | 1.42 | 1.63 | 1.53 |
| | 48 h | 1.65 | 1.51 | 1.78 | 1.65 |
| PP1 | 0 h | 0.28 | 0.35 | 0.41 | 0.35 |
| | 12 h | 0.52 | 0.66 | 0.42 | 0.53 |
| | 24 h | 1.24 | 1.07 | 1.48 | 1.26 |
| | 36 h | 1.77 | 1.62 | 1.81 | 1.73 |
| | 48 h | 1.96 | 1.78 | 2.10 | 1.95 |
| PP2 | 0 h | 0.41 | 0.24 | 0.33 | 0.33 |
| | 12 h | 0.49 | 0.6 | 0.37 | 0.49 |
| | 24 h | 1.57 | 1.78 | 1.62 | 1.66 |
| | 36 h | 2.31 | 2.14 | 1.98 | 2.14 |
| | 48 h | 2.39 | 2.07 | 2.56 | 2.34 |
| PP3 | 0 h | 0.36 | 0.52 | 0.27 | 0.38 |
| | 12 h | 0.42 | 0.51 | 0.56 | 0.50 |
| | 24 h | 1.08 | 1.62 | 1.32 | 1.34 |
| | 36 h | 1.95 | 1.83 | 1.74 | 1.84 |
| | 48 h | 2.07 | 2.32 | 1.95 | 2.11 |
| PP4 | 0 h | 0.41 | 0.37 | 0.22 | 0.33 |
| | 12 h | 0.54 | 0.45 | 0.68 | 0.56 |

TABLE 6-continued

Effects of different polypeptide fractions
on proliferation of C2C12 cells

| Group | Treatment time | Repeated three groups | | | Average value |
|---|---|---|---|---|---|
|  | 24 h | 1.31 | 1.06 | 1.62 | 1.33 |
|  | 36 h | 2.03 | 1.67 | 1.89 | 1.86 |
|  | 48 h | 1.87 | 2.11 | 2.28 | 2.09 |
| PP5 | 0 h | 0.44 | 0.27 | 0.36 | 0.36 |
|  | 12 h | 0.43 | 0.53 | 0.71 | 0.557 |
|  | 24 h | 1.41 | 1.66 | 1.19 | 1.42 |
|  | 36 h | 1.72 | 2.06 | 1.86 | 1.88 |
|  | 48 h | 1.98 | 2.32 | 2.05 | 2.12 |

Plotting was conducted against the average values of each group, as shown in FIG. 6. The results show that when the samples (PP1, PP2, PP3, PP4 or PP5) were added and incubated with the C2C12 cells for 12 h, the cell concentrations of the sample groups were similar to that of CN group. However, when co-incubated for 24 h or 36 h, the cell concentration in PP2 group increases significantly compared with that in the CN group; when co-incubated for 48 h, the cell concentration in the sample group (PP1, PP2, PP3, PP4 or PP5) increases significantly compared with that in the CN group; where PP2 sample group has the best effect on promoting the proliferation of C2C12 cells.

Activation of Growth and Proliferation Signaling Pathways in C2C12 Cells by Five Pea-Derived Peptides The effects of five pea-derived peptides on growth and proliferation signaling pathways in C2C12 cells were further investigated. The results show that after co-incubating the pea-derived peptide sample (PP1, PP2, PP3, PP4 or PP5) for 24 h, PP2 sample group has the best muscle-building effect. Correspondingly, the western blot analysis (FIG. 7 and FIG. 8A-FIG. 8D) also shows that co-culture of PP2 more significantly enhances the activation of the growth signaling pathway p-AMPK/IGF-1/IGF-1R in C2C12 cells compared to the control group (CN). In addition, PP2 also significantly up-regulates the expression of key regulatory proteins CyclinD1 and CDK6 in a G0/S phase of the cell cycle, promoting cell cycle progression, which is why PP2 better promotes the proliferation of C2C12 cells. In conclusion, the results suggest that PP2 significantly up-regulates the expression of cyclin, promotes the cycle progression of C2C12 cells, and also activates the growth signaling pathway, thereby ultimately promoting the proliferation of C2C12 cells. The activation of these signaling pathways is an important part of promoting muscle growth, such that the oligopeptide PP2 has a more obvious muscle-building effect than several other oligopeptides. In addition, the oligopeptide with the amino acid sequence of PP2 (LDLPVL) was more pronounced in the proliferation of C2C12 cells than other oligopeptides.

Example 3

Figure 9:
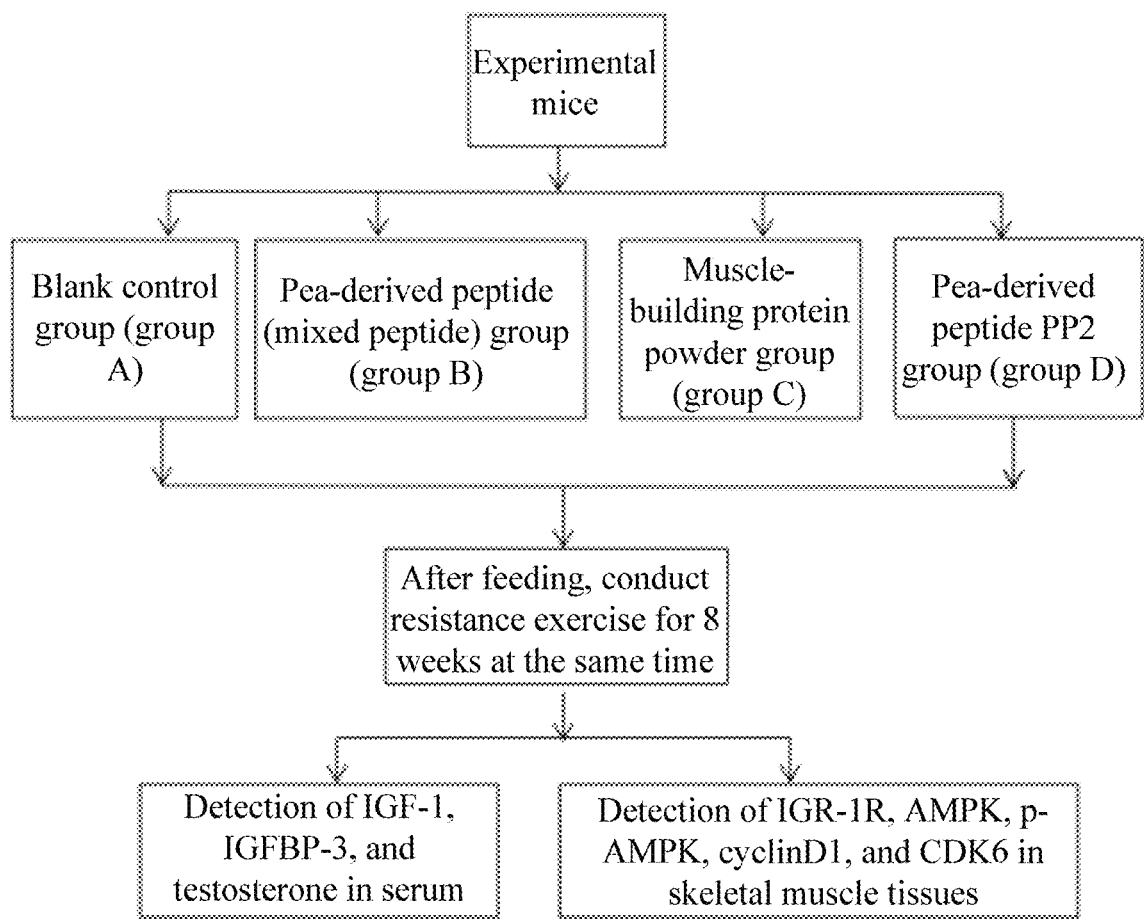
FIG. 9 shows an experimental flow chart of sarcopenia model mice in the examples of the present disclosure.

Pea-derived peptide is a high-quality polypeptide that has been widely used in the field of fitness and bodybuilding, and is especially favored by vegetarian fitness and fitness enthusiasts. Compared with soybean polypeptides, the pea-derived peptides are rich in branched-chain amino acids. Therefore, from the perspective of muscle building, pea-derived peptides have better effects. In this example, the purpose was to determine the muscle-building effect of the pea-derived peptide prepared above for a long time, and to preliminarily explore its mechanism of action. A specific experimental process is shown in FIG. 9.

Experimental Materials and Methods 1.1. Experimental Schemes

In this experiment, SPF-grade C57 mice were used as model mice, and were randomly divided into 4 groups: a normal control group (group A, the mice were given normal saline with 0.4 g/kg body weight every day by gavage), a pea-derived peptide (peptide prepared in Example 1) group (group B), a muscle-building protein powder group (group C), and a pea-derived peptide PP2 group (group D). Each experimental group was subjected to 8 weeks of ladder climbing resistance exercise with weight loaded on the mice. Mice in the pea-derived peptide group were given 0.4 g/kg body weight of pea-derived peptide daily by gavage, and underwent resistance exercise training; mice in the muscle-building protein powder group (group C) were given 1.0 g/kg body weight of a muscle-building protein powder daily by gavage, and underwent resistance exercise training; mice in the pea-derived peptide PP2 group (group D) were given 0.1 g/kg body weight of pea-derived peptide daily by gavage, and underwent resistance exercise training; and mice in the CN group were given an equal volume of normal saline daily without undergoing resistance exercise training. The muscle-building principle of resistance exercise training is a continuous destruction, repair and regeneration process of muscle fibers (muscle cells). A specific exercise program was as follows: after being familiar with a ladder for one week, the mice in the sample groups underwent a ladder climbing exercise on a 1-m ladder for 8 weeks, where the ladder was inclined at 85°, and the 2-cm grid ladder was attached with weights to the mouse tail. A maximum load that could be successfully loaded over the entire length of the ladder was considered a maximum load capacity of the training session, and the maximum load capacity was detected in the first 1, 2, 4, 6 and 8 weeks separately. Each mouse was loaded with 50% of its body weight during the first training week, and the exercise load was increased to 100% of its body weight until the end of week 8; where a frequency was set to 3 times per week, with a rest period of 60 seconds between repetitions and 5-min rest intervals between sessions. The grip strength of forelimbs before and after the experiment was measured. At the end of the experiment, the experimental mice were sacrificed, and the serum and rectus femoris were taken for later use.

1.2. Determination of Gripping Strength

The experimental mice were grasped and placed on a grip strength plate with the right hand, a tension plate was pushed forward with the left hand, and the right hand slid back to the tail The mice were pulled back in time when the mice grasped the grip strength plate hard to an extent that the maximum grip strength of the mice can be measured.

1.3. Determination of Testosterone, IGF-1 and IGFBP-3

The experimental mouse serum was taken to measure the content of testosterone, IGF-1 and IGFBP-3 separately according to operating instructions of an enzyme-linked immunosorbent assay (ELISA) kit.

1.4. Determination of ATPase Activity

Icy normal saline was added to a fresh muscle tissue, and liver tissues were cut up as soon as possible with a small ophthalmic scissors. The minced muscle tissue was poured into a glass homogenization tube, the fragments of tissue remaining in a beaker were rinsed using the remaining ⅓ cold normal saline, and poured into the homogenization tube together for homogenization. The lower end of the homogenization tube was inserted into the beaker containing an ice-water mixture with the left hand, and a ramming rod was inserted vertically into a casing with the right hand; grinding was thoroughly conducted by rotating up and down for dozens of times (6 min to 8 min) to homogenize the muscle tissue (10% tissue homogenate). Centrifugation was conducted to separate the supernatant, and the ATPase activity in the mitochondria of rectus femoris tissue was determined according to the steps of an ATPase kit operating instruction.

1.5. Effects of Samples on Insulin Signaling Pathway

Insulin signaling pathway is important in the muscle growth. In this study, effects of the pea-derived peptide on the insulin signaling pathway were detected using the Western blot. The operation method specifically includes: triceps surae of an experimental mouse was homogenized, cells were sonicated, a loading buffer was added to a supernatant, 12% SDS-PAGE protein separation was conducted, and electroporation was conducted at 350 mA for 2.5 h, a PVDF membrane was taken out, and was blocked with a 5% skimmed milk powder at room temperature for 1 hour, the membrane was washed with a TBS-T for 3 times, a primary antibody was incubated overnight at 4° C., the membrane was washed with TBS-T for 3 times, a secondary antibody was incubated at room temperature for 1 hour, the membrane was washed, and an ECL luminescent agent was added to develop color.

2. Results and Discussion 2.1. Samples can Improve a Forelimb Gripping Strength of Mice

TABLE 7

Results of forelimb gripping strength in mice

| Item | Group A | Group B | Group C | Group D |
|---|---|---|---|---|
| Initial grip strength (g) | 142.6 ± 12.5 | 151.3 ± 15.6 | 147.7 ± 16.1 | 149.2 ± 15.4 |
| 8 weeks after | 212 ± 25.7 | 273.8 ± 31.5 | 254.5 ± 27.3 | 292.6 ± 35.4 |

Figure 10:
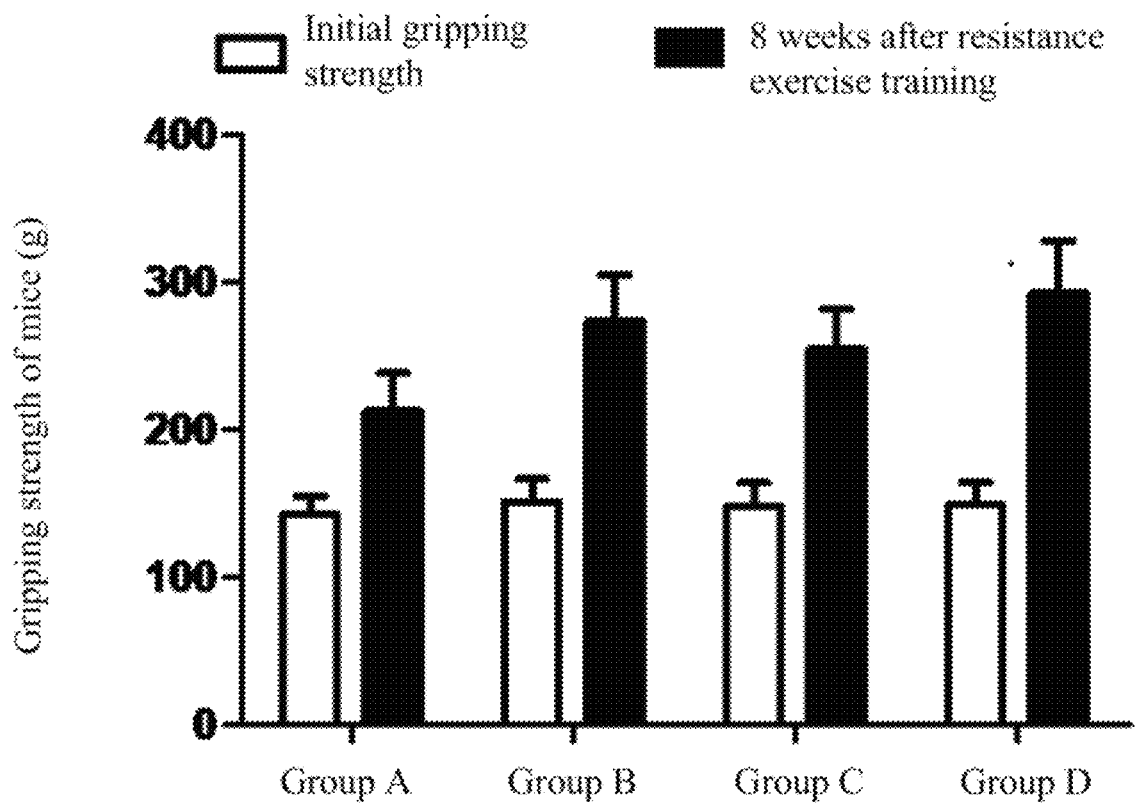
FIG. 10 shows a result of the pea-derived peptide samples improving a forelimb gripping force of the mice in the examples of the present disclosure.

From results of measuring the forelimb gripping force of mice (Table 7), it is found that the pea-derived peptide PP2 group (group D) can significantly improve the forelimb gripping strength of mice, producing an effect better than those in the muscle-building protein powder group (group C) and the pea-derived peptide (mixed peptide) group (group B). Compared with the normal control group (group A), the group B, group C and group D each can improve the forelimb gripping strength of mice (FIG. 10).

2.2. Samples can Increase Testosterone Levels in Mice

Figure 11:
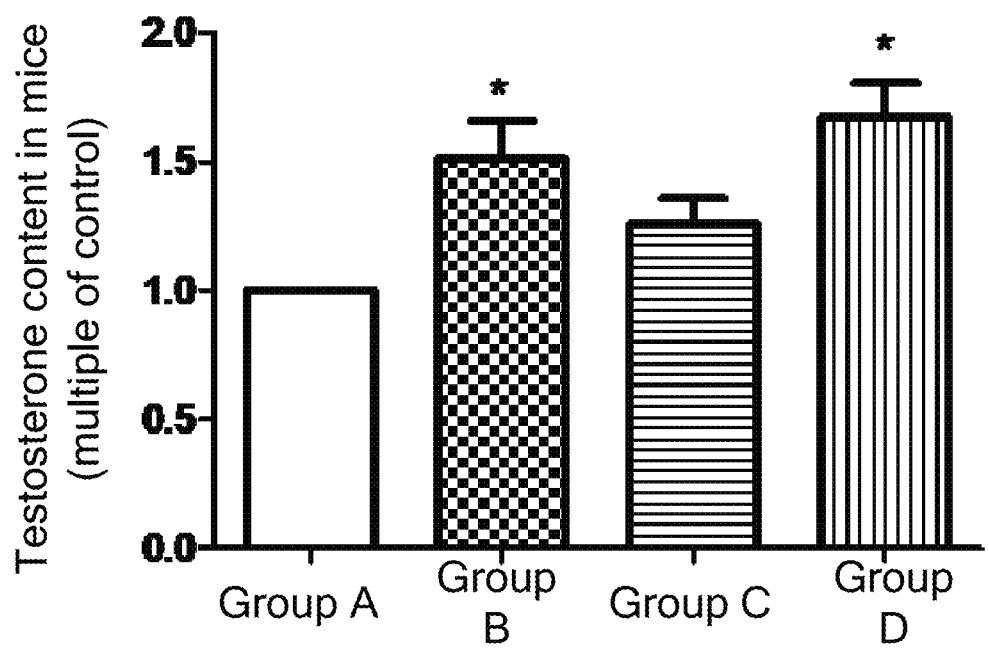
FIG. 11 shows statistical results of the pea-derived peptide samples increasing a testosterone level of the mice in the examples of the present disclosure.

Testosterone is very closely related to muscle growth, and high-level testosterone can significantly reduce protein degradation. Moreover, increasing the testosterone level can effectively reduce fat. The experimental results are shown in FIG. 11, where the horizontal axis represents the different treatment groups, and the vertical axis represents a control multiple; the control multiple is a multiple for testosterone increase of the mice in group B, group C and group D based on the normal group undergoing muscle-building training. Testosterone is a steroid hormone secreted by testicles of males or ovaries of females, and a small amount of testosterone is also secreted by adrenal glands. Testosterone has the functions of maintaining muscle strength and mass, maintaining bone density and strength, refreshing, and improving physical performances. Compared with the control group, taking pea-derived peptide (mixed peptide in an equal mass) group (group B) and pea-derived peptide PP2 group (group D) can significantly increase the testosterone levels of mice, and the testosterone level is significantly higher than that in mice intaking the muscle-building powder. The effect of intaking the pea-derived peptide (mixed peptide) group (group B) and the pea-derived peptide PP2 group (group D) for testosterone increase is better than that of simply intaking the muscle-building protein powder group (group C).

2.3. Pea-Derived Peptide can Increase Content of IGF-1 in Serum of Mice

Figure 12:
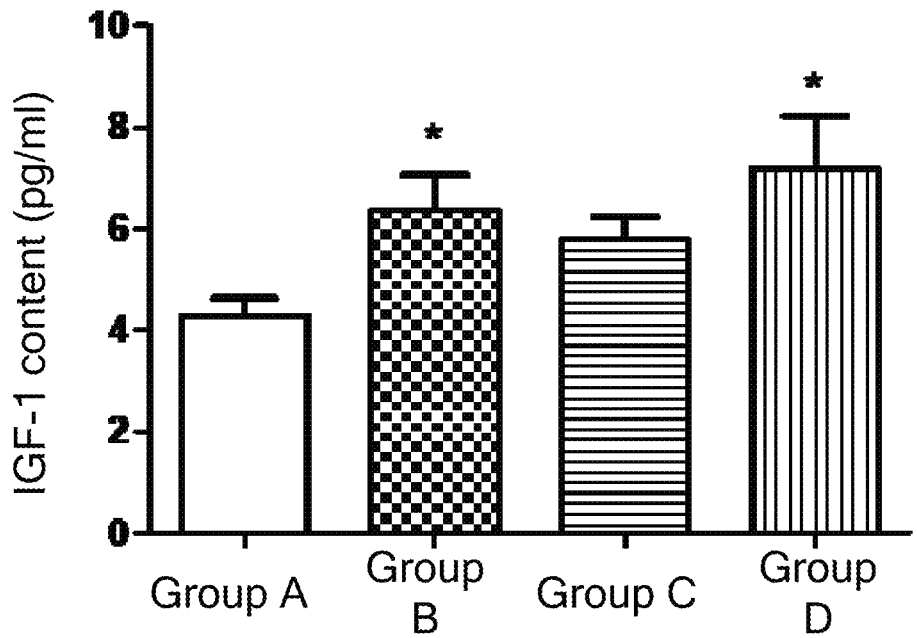
FIG. 12 shows statistical results of the pea-derived peptide samples increasing an IGF-1 content of the mice serum in the examples of the present disclosure.

IGF-1 is a key positive regulator in the skeletal muscle regeneration and is important in promoting the skeletal muscle growth. The results show that compared with the control group, intaking the pea-derived peptide (mixed peptide) group (group B) and the pea-derived peptide PP2 group (group D) can significantly increase the content of IGF-1 in the peripheral blood of mice, with an increase higher than that in the muscle-building protein powder group (group C) (FIG. 12).

2.4. Samples can Reduce Content of IGFBP-3 in Serum of Mice

Figure 13:
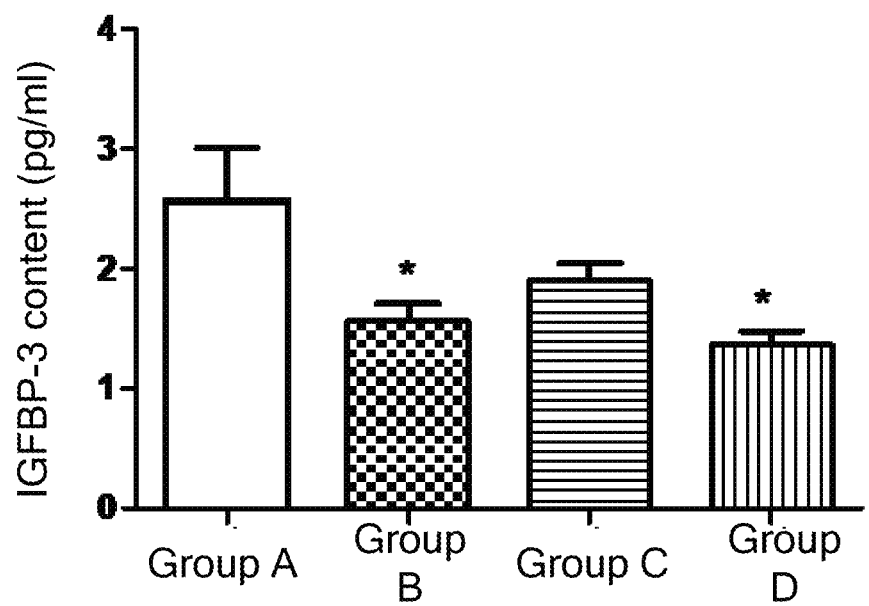
FIG. 13 shows statistical results of the pea-derived peptide samples increasing an IGFBP-3 content of the mice serum in the examples of the present disclosure.

IGFBP is an IGFs binding protein; when binding to IGF-1 or IGF-2, the IGFBP can hinder the IGFs signaling pathway; IGFBP-3 is the most important one of the IGFBP species, and other IGF-1 have high affinity. After 8 weeks of resistance exercise training, the level of IGFBP-3 in the peripheral blood of experimental mice in the pea-derived peptide (mixed peptide) group (group B) and the pea-derived peptide PP2 group (group D) is significantly lower than that in the normal control group (Group A), and also lower than that in the muscle-building protein powder group (Group C) (FIG. 13).

2.5. The Samples can Increase ATPase Activity in Skeletal Muscle Mitochondria

Figure 14:
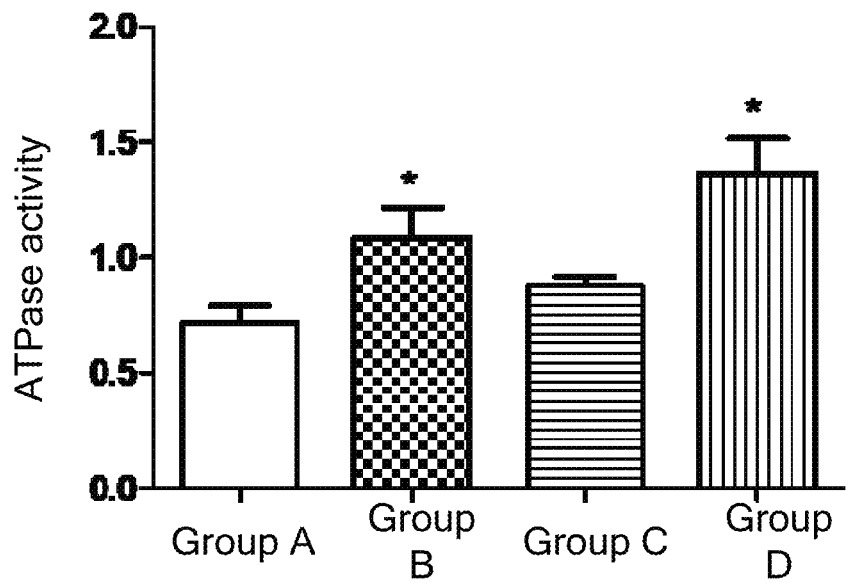
FIG. 14 shows that the pea-derived peptide samples increase ATPase activity in skeletal muscle mitochondria in the examples of the present disclosure.

Mitochondria are the main place to synthesize ATP, and ATP is the energy required for body movement. A high-energy phosphate bond may be hydrolyzed by an ATP hydrolase to generate a free ATP to provide energy for body activities. From the experimental results, compared with the control group and the muscle-building protein powder group, intaking the pea-derived peptide (mixed peptide) group (group B) and the pea-derived peptide PP2 group (group D) can significantly increase ATP hydrolase activity in skeletal muscle mitochondria, and the ATP hydrolase activity is also higher than that in the muscle-building protein powder group (group C) (FIG. 14).

2.6 The Samples can Activate IGF/IGF-1R Signaling Pathways

Figure 15:
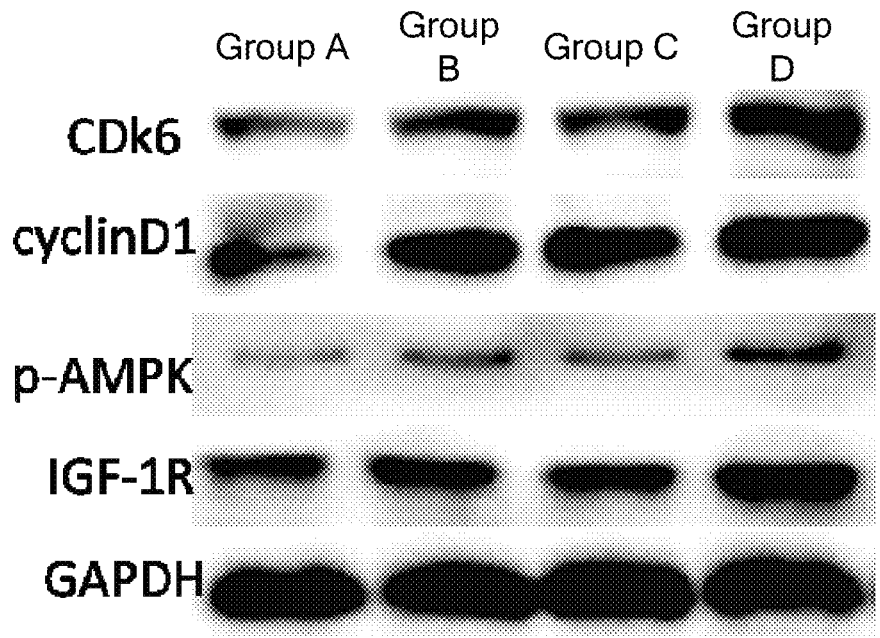
FIG. 15 shows a result of activation of an IGF/IGF-1R signaling pathway by the pea-derived peptide samples in the examples of the present disclosure.

Insulin-like growth factors (IGFs) signaling pathway plays an important role in muscle growth and injury repair. To investigate the activation of the IGFs signaling pathway by the samples, the expression of IGFs signaling pathway-related proteins was examined by western blot. The results show that, compared with the normal control group (group A), the band width and color of IGF-1R in the pea-derived peptide PP2 group (group D) are significantly and wider deeper than those obtained in the control group (FIG. 15). This indicates that the expression of IGF-1R in C2C12 cells is significantly increased after stimulation with PP2 compared with the control group (without co-incubation of PP2). IGF-1R is a receptor for IGF-1; after the IGF-1 binds to the IGF-1R, activation of downstream growth signals is initiated An increase in the expression level of IGF-1R means a higher degree of growth signal activation, which promotes the phosphorylation of AMPK, and then induces the up-regulation of cell cycle-related proteins cyclinD1 and CDK6, thereby eventually leading to cell proliferation. When the pea-derived peptide PP2 was given at the same time, the IGFs signaling pathway can be better activated.

Example 4

In Vitro Digestion Test of Pea-Derived Peptide (the Mixed Peptide Prepared in Example 1)

A pea-derived peptide aqueous solution and a pea-derived peptide PP2 aqueous solution with a mass concentration of 500 mg/L were prepared separately, pepsin (20 mg/g) was added, a pH value was adjusted to 2.0, and the two aqueous solutions were treated in a water bath at a constant temperature of 37° C. for 90 min. Following the water bath, the pH value was adjusted to 7.5, trypsin (40 mg/g) was added, and the two aqueous solutions were treated in the water bath at a constant temperature of 37° C. for 150 min. Following the water bath, the two solutions were placed in a 95° C. water bath for 5 min to inactivate the enzyme. The samples were freeze-dried and analyzed by HPLC to compare changes in the liquid chromatograms before and after digestion. Also provided were undigested pea-derived peptide and pea-derived peptide digested only by pepsin but not by trypsin.

Figure 16:
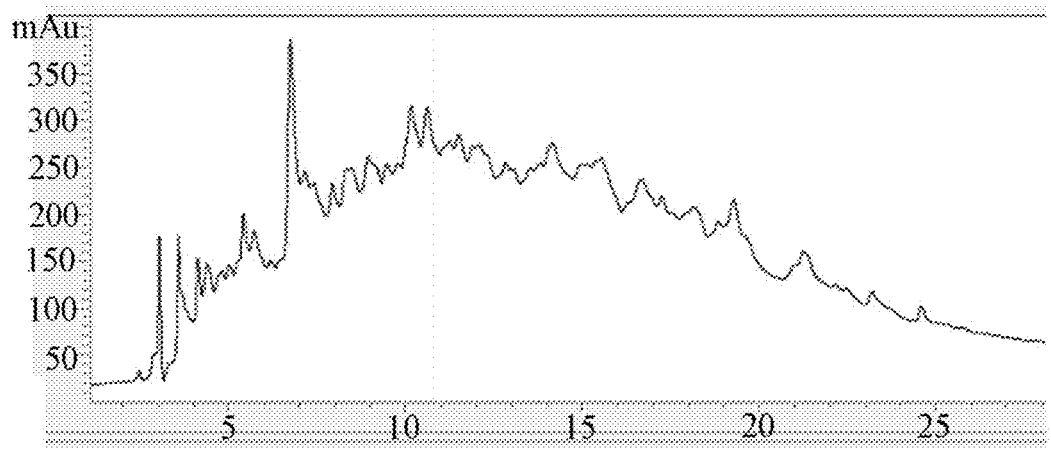
FIG. 16 shows a liquid chromatogram of an undigested pea-derived peptide, where a horizontal axis represents time in min; and a vertical axis value is expressed in mAU.
Figure 17:
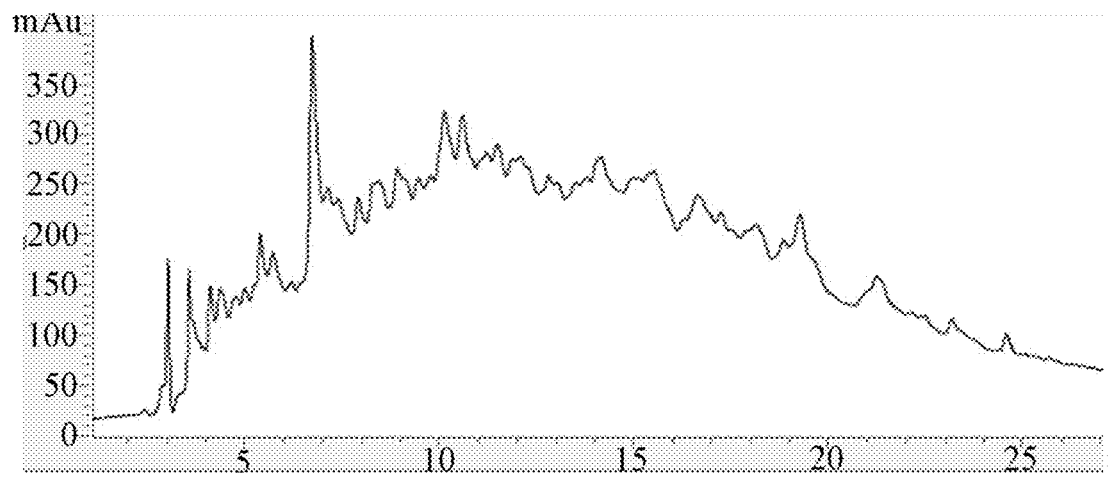
FIG. 17 shows a liquid chromatogram of the pea-derived peptide digested by pepsin, where a horizontal axis represents time in min; and a vertical axis value is in expressed mAU.
Figure 18:
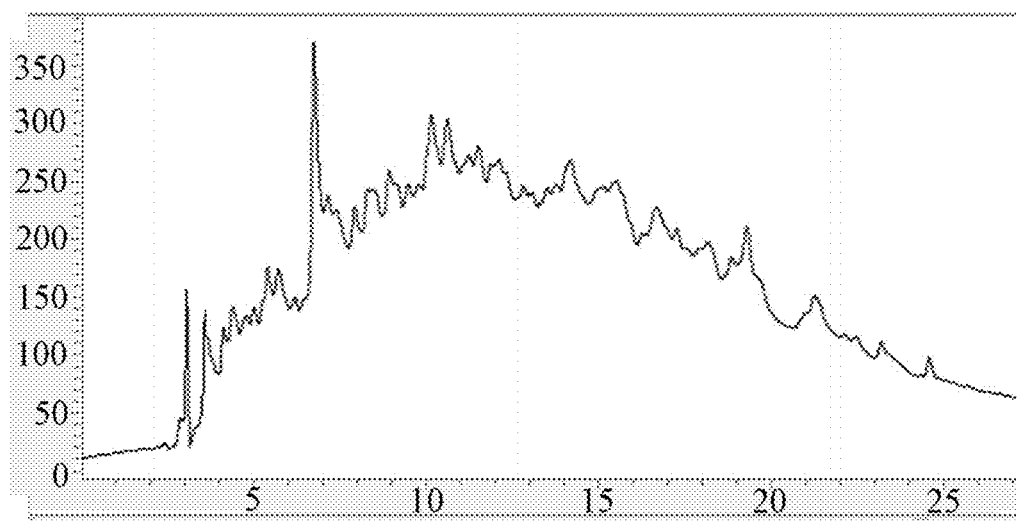
FIG. 18 shows a liquid chromatogram of the pea-derived peptide digested by pepsin and trypsin, where a horizontal axis represents time in min; and a vertical axis value is expressed in mAU.
Figure 19:
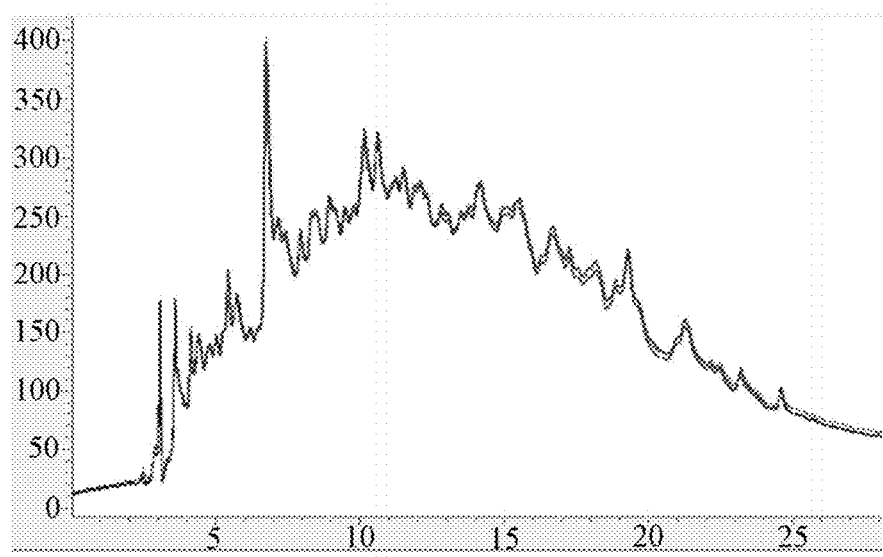
FIG. 19 shows comparison of superposition of the liquid chromatograms under the three conditions, where a horizontal axis represents time in min; and a vertical axis value is expressed in mAU.

The undigested samples, pepsin-digested samples, pepsin and trypsin-digested samples for the pea-derived peptide were analyzed by HPLC. The results are shown in FIG. 16 to FIG. 18, and a three-figure overlapping fitting result is shown in FIG. 19. The peak time, signal strength, and peak shape were compared for different groups. After pea-derived peptide was digested by pepsin and trypsin, compared with the liquid chromatogram of pea-derived peptide without protease treatment, there is no obvious increase or decrease in chromatographic peaks in the liquid chromatograms of other treatment groups, and a peak shape and a peak time are not significantly changed. This indicates that after being digested by pepsin and trypsin, the pea-derived peptide basically maintains the original composition and characteristics, with desirable stability.

Example 5

Figure 20:
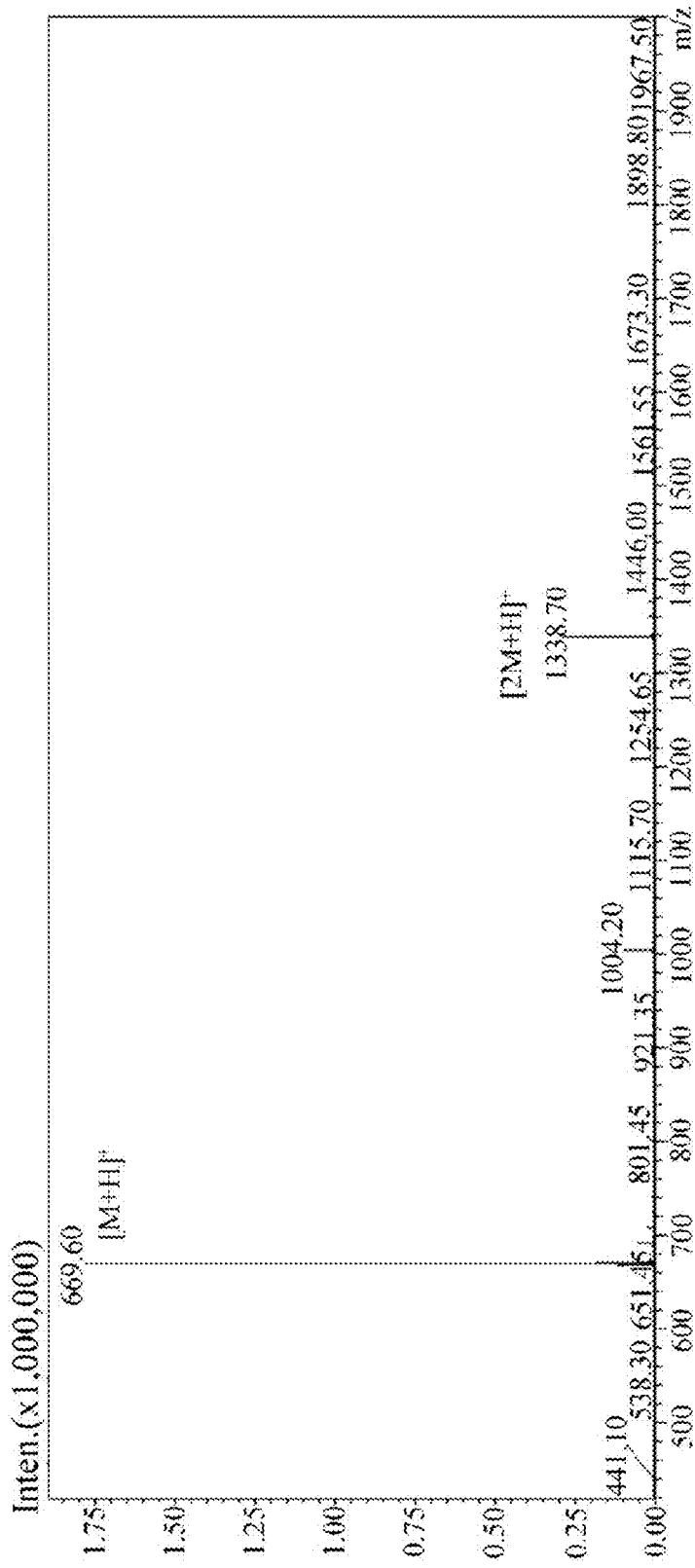
FIG. 20 shows results of an in vitro digestion test of the fraction PP2.

Pea-derived peptide PP2 was digested in vitro according to the method of Example 4. The pea-derived peptide PP2 was detected by liquid chromatography-mass spectrometry, and the results are shown in FIG. 20. PP2 has a molecular weight of 668.82, which is basically consistent with 669.6 in FIG. 20 (one charge is added, and the actual molecular weight is that is subtracted by one), indicating that the fraction PP2 is not digested and degraded by the pepsin and trypsin.

The above description is merely preferred implementations of the present disclosure. It should be noted that a person of ordinary skill in the art may further make several improvements and modifications without departing from the principle of the present disclosure, and such improvements and modifications should be deemed as falling within the protection scope of the present disclosure.

What is claimed is:

1. A method for preparing a pea-derived peptide comprising one or more of the following polypeptides as separate peptide fragments: PP1 with an amino acid sequence shown in SEQ ID NO: 1, PP2 with an amino acid sequence shown in SEQ ID NO: 2, PP3 with an amino acid sequence shown in SEQ ID NO: 3, PP4 with an amino acid sequence shown in SEQ ID NO: 4, and PP5 with an amino acid sequence shown in SEQ ID NO: 5, wherein the method comprises the following steps:
   1) conducting enzymatic hydrolysis on a pea protein under an action of an alkaline protease to obtain a first enzymatic hydrolysate;
   2) conducting enzymatic hydrolysis on the first enzymatic hydrolysate under an action of papain and cellulase to obtain a second enzymatic hydrolysate;
   3) inactivating the second enzymatic hydrolysate, then filtering inactivated second enzymatic hydrolysate through a ceramic membrane, filtering through an organic membrane, and collecting a permeate to obtain a pea-derived peptide;
   4) subjecting the pea-derived peptide to gel chromatography, and collecting a fraction S2 12-18 min;
   5) subjecting the fraction S2 to separation and purification by preparative liquid chromatography, and collecting a fraction W5 at 55-63 min; and
   6) subjecting the fraction W5 to separation and purification by analytical liquid chromatography, and sequentially collecting 5 polypeptide fragments at a PP1 time interval, a PP2 time interval, a PP3 time interval, a PP4 time interval, and a PP5 time interval, respectively, to obtain PP1, PP2, PP3, PP4, and PP5.

2. The method according to claim 1, wherein in step 4), the gel chromatography is conducted by:
   using ultrapure water as an eluent in a chromatographic column.

3. The method according to claim 1, wherein in step 5), the separation and purification by preparative liquid chromatography is specifically conducted using a preparative liquid chromatographic column at a predetermined flow rate using a mobile phase A comprising a trifluoroacetic acid aqueous solution, and a mobile phase B comprising a trifluoroacetic acid acetonitrile solution; and a gradient elution process including the steps of:
   eluting from 0 min to 10 min, with a volume percentage of the mobile phase A decreased from 100% to 90%, and a volume percentage of the mobile phase B increased from 0 to 10%;
   eluting from 10 min to 20 min, with a volume percentage of the mobile phase A decreased from 90% to 50%, and a volume percentage of the mobile phase B increased from 10% to 50%;
   eluting from 20 min to 60 min, with a volume percentage of the mobile phase A decreased from 50% to 10%, and a volume percentage of the mobile phase B increased from 50% to 90%;
   eluting from 60 min to 65 min, with a volume percentage of the mobile phase A increased from 10% to 95%, and a volume percentage of the mobile phase B decreased from 90% to 5%; and
   eluting from 65 min to 100 min, with a volume percentage of the mobile phase A at 95%, and a volume percentage of the mobile phase B at 5%.

4. The method according to claim 1, wherein in step 6), the separation and purification by analytical liquid chromatography is specifically conducted under the following conditions: a chromatographic column at a predetermined flow rate using a mobile phase A comprising a trifluoroacetic acid aqueous solution %, and a mobile phase B comprising a trifluoroacetic acid acetonitrile solution; and a gradient elution process including the steps of:
   eluting from 0 min to 5 min, with a volume percentage of the mobile phase A decreased from 95% to 90%, and a volume percentage of the mobile phase B increased from 5% to 10%;
   eluting from 5 min to 55 min, with a volume percentage of the mobile phase A decreased from 90% to 15%, and a volume percentage of the mobile phase B increased from 10% to 85%; and
   eluting from 55 min to 60 min, with a volume percentage of the mobile phase A increased from 15% to 95%, and a volume percentage of the mobile phase B decreased from 85% to 5%.

5. The method according to claim 2, wherein:
   in step 3) the second enzymatic hydrolysate is filtered through a ceramic membrane of 3,000 Da and filtered through an organic membrane of 1 KDa;
   in step 6) the PP1 time interval is 14.444 min, the PP2 time interval is 18.110 min, the PP3 time interval is 20.906 min, the PP4 time interval is 22.973 min, and the PP5 time interval is 24.462 min.

6. The method according to claim 5, wherein in step 4), the gel chromatography is conducted using ultrapure water as an eluent for elution at 2.5 mL/min for 2 h by using a Sephadex G50 chromatographic column of 600 mm×25 mm under a detection wavelength of 214 nm.

7. The method according to claim 5, wherein in step 5), the preparative liquid chromatographic column is a 550 mm×40 μm column with a particle size of 20 μm, the predetermined flow rate is 15 mL/min, the trifluoroacetic acid aqueous solution has a volume concentration of 0.1%, and the trifluoroacetic acid acetonitrile solution has a volume concentration of 0.1%.

8. The method according to claim 5, wherein in step 6), the separation and purification by analytical chromatography is conducted using a 10 μm C18 100A 4.6×250 mm chromatographic column, the predetermined flow rate is 15 mL/min, the trifluoroacetic acid aqueous solution has a volume concentration of 0.1%, and the trifluoroacetic acid acetonitrile solution has a volume concentration of 0.1%; wherein the chromatographic column is operated at a flow rate of 1.0 mL/min with an injection volume of 10 μL, and an absorbance wavelength of 220 nm.

9. A drug for treating sarcopenia having active ingredients that comprise a pea-derived peptide prepared by the method according to claim 1.

10. A drug for treating sarcopenia having active ingredients that comprise a pea-derived peptide prepared by the method according to claim 2.

11. A drug for treating sarcopenia having active ingredients that comprise a pea-derived peptide prepared by the method according to claim 3.

12. A drug for treating sarcopenia having active ingredients that comprise a pea-derived peptide prepared by the method according to claim 4.

13. A drug for treating sarcopenia having active ingredients that comprise a pea-derived peptide prepared by the method according to claim 5.

14. A drug for treating sarcopenia having active ingredients that comprise a pea-derived peptide prepared by the method according to claim 6.

15. A drug for treating sarcopenia having active ingredients that comprise a pea-derived peptide prepared by the method according to claim 7.

* * * * *

SEQUENCE LISTING

```
Sequence total quantity: 5
SEQ ID NO: 1          moltype = AA  length = 8
FEATURE               Location/Qualifiers
REGION                1..8
                      note = amino acid sequence of PP1
source                1..8
                      mol_type = protein
                      organism = synthetic construct
SEQUENCE: 1
EGSLLLPH                                                                 8

SEQ ID NO: 2          moltype = AA  length = 6
FEATURE               Location/Qualifiers
REGION                1..6
                      note = amino acid sequence of PP2
source                1..6
                      mol_type = protein
                      organism = synthetic construct
SEQUENCE: 2
LDLPVL                                                                   6

SEQ ID NO: 3          moltype = AA  length = 6
FEATURE               Location/Qualifiers
REGION                1..6
                      note = amino acid sequence of PP3
source                1..6
                      mol_type = protein
                      organism = synthetic construct
SEQUENCE: 3
LLYVIR                                                                   6

SEQ ID NO: 4          moltype = AA  length = 11
FEATURE               Location/Qualifiers
REGION                1..11
                      note = amino acid sequence of PP4
source                1..11
                      mol_type = protein
                      organism = synthetic construct
```

```
-continued

SEQUENCE: 4
TNYEEIEKVL L                                                              11

SEQ ID NO: 5         moltype = AA  length = 11
FEATURE              Location/Qualifiers
REGION               1..11
                     note = amino acid sequence of PP5
source               1..11
                     mol_type = protein
                     organism = synthetic construct
SEQUENCE: 5
NTNYEEIEKV L                                                              11
```